US012600973B2

(12) United States Patent
Wang et al.

(10) Patent No.: US 12,600,973 B2
(45) Date of Patent: Apr. 14, 2026

(54) CpG ODN HAVING IMMUNOREGULATORY FUNCTION AND USE THEREOF

(71) Applicant: PARR BIOTECHNOLOGY (HEBEI) CO., LTD., Shijiazhuang City (CN)

(72) Inventors: Ligong Wang, Shijiazhuang City (CN); Yan Shao, Shijiazhuang City (CN)

(73) Assignee: Parr Biotechnology (Hebei) Co., Ltd., Shijiazhuang City (CN)

( * ) Notice: Subject to any disclaimer, the term of this patent is extended or adjusted under 35 U.S.C. 154(b) by 818 days.

(21) Appl. No.: 17/915,805

(22) PCT Filed: Mar. 31, 2021

(86) PCT No.: PCT/CN2021/084467

§ 371 (c)(1),
(2) Date: Sep. 29, 2022

(87) PCT Pub. No.: WO2021/197381

PCT Pub. Date: Oct. 7, 2021

(65) Prior Publication Data

US 2023/0159936 A1 May 25, 2023

(30) Foreign Application Priority Data

Apr. 1, 2020 (CN) ......................... 202010253089.8

(51) Int. Cl.

| | |
|---|---|
| ***C12N 15/117*** | (2010.01) |
| ***A61K 39/00*** | (2006.01) |
| ***A61K 39/205*** | (2006.01) |
| ***A61K 39/215*** | (2006.01) |
| ***A61K 39/39*** | (2006.01) |
| ***A61P 31/14*** | (2006.01) |

(52) U.S. Cl.

CPC .... *C12N 15/117* (2013.01); *A61K 39/001156* (2018.08); *A61K 39/001192* (2018.08); *A61K 39/205* (2013.01); *A61K 39/215* (2013.01); *A61K 39/39* (2013.01); *A61P 31/14* (2018.01); *A61K 2039/55505* (2013.01); *A61K 2039/55561* (2013.01); *C12N 2310/17* (2013.01); *C12N 2310/315* (2013.01)

(58) Field of Classification Search

None

See application file for complete search history.

(56) References Cited

U.S. PATENT DOCUMENTS 7,491,706 B2 * 2/2009 Yu .......................... A61P 31/14
424/193.1
10,052,378 B2 * 8/2018 Wang ...................... C12N 7/00

FOREIGN PATENT DOCUMENTS

CN 1271733 A * 11/2000
CN 1678188 A 10/2005
CN 101094594 A 12/2007
JP 2019163302 A 9/2019
JP 2019172701 A 10/2019
WO 2019115385 A1 6/2019

OTHER PUBLICATIONS

Zhou, Peng, et al. "A pneumonia outbreak associated with a new coronavirus of probable bat origin." Nature 579.7798 (Feb. 2020): 270-273. (Year: 2020).*

Tokunaga et al., Antitumor activity of deoxyribonucleic acid fraction from *Mycobacterium bovis* BCG. I. isolation, physicochemical characterization, and antitumor activity, J Natl Cancer Inst, 1984, 72(4): 955-962.

Tokunaga et al., A synthetic single stranded DNA, Poly(dG, dC), induces interferon-alpha/beta and -gamma, augments natural killer activity, and suppresses tumor growth, Jpn J Cancer Res, 1988, 79(6): 682-686.

Tokunaga et al., Synthetic oligonucleotides with particular base sequences from the cDNA encoding proteins of *Mycobacterium bovis* BCG induce interferons and activate natural killer cells, Microbiol Immunol, 1992, 36(1): 55-66.

Ling et al., Research development of immunoactive CpG oligodeoxynucleotides, Chinese Journal of Microbiology and Immunology, 2008, 28(6): 571-576.

Krieg et al., CpG motifs in bacterial DNA trigger direct B-cell activation, Nature, 1995, 374(6522): 546-549.

Ballas et al., Induction of NK activity in murine and human cells by CpG motifs in oligodeoxynucleotides and bacterial DNA, J Immunol, 1996, 157(5): 1840-1845.

Hartmann et al., Mechanism and function of a newly identified CpG DNA motif in human primary B cells, J Immunol, 2000, 164(2): 944-953.

Xu et al., Delineation of CpG motifs for activating human immune cells, Chinese Journal of Microbiology and Immunology, 2001, 21(5): 471-475.

Krieg et al., Mechanism of action of CpG DNA, Current Topics in Microbiology and Immunology, 2000, 247(1).

Mutwiri et al., Biological activity of immunostimulatory CpG DNA motif in domestic animals, Veterinary Immunology and Immunopathology, 2003, 91: 89-103.

Ahlers et al., Memories that last forever: strategies for optimizing vaccine T-cell memory, Blood, 2010, 115(9): 1678-1689.

Sun et al., Type I interferon-mediated stimulation of T cells by CpG DNA, J. Exp Med, 1998, 188(12): 2335-2342.

Krieg, Therapeutic potential of Toll-like receptor 9 activation, Nat Rev Drug Discov, 2006, 5(6): 471-484.

(Continued)

*Primary Examiner* — Bethany P Barham
*Assistant Examiner* — Peter Anthopolos
(74) *Attorney, Agent, or Firm* — Medler Ferro Woodhouse & Mills PLLC

(57) ABSTRACT

Provided are an immunomodulatory CpG ODN chemically modified by means of a structure as shown by general formula I and the use thereof. The CpG ODN has an immunostimulatory activity, can stimulate the proliferation of B cells, and produce specific cytokines. The above-mentioned CpG ODN can be used as a vaccine adjuvant alone or in combination with other adjuvants to exert a synergistic effect, and can also be used in the preparation of drugs for preventing or treating tumors, infections, and allergies.

22 Claims, 10 Drawing Sheets

Specification includes a Sequence Listing.

(56) References Cited

OTHER PUBLICATIONS

Klinman, CpG DNA as a vaccine adjuvant, Expert Rev Vaccines, 2003, 2(2): 305-315.
Krieg, CpG still rocks! Update on an accidental drug, Nucleic Acid Ther, 2012, 22(2): 77-89.
Liu et al., Study on anti-HBV effects by antisense oligodeoxynucleotides in vitro, China Journal of Preventive Medicine, 2001, 35(5): 338-340.
Lund et al., Inhibition of HIV-1 replication by chimeric phosphorothioate oligodeoxynucleotides applied in free solution, Intervirology, 1998, 41(2-3): 63-68.
Speiser et al., Rapid and strong human CD8(+) T cell responses to vaccination with peptide, IFA, and CPG oligodeoxynucleotide 7909, J Clin Invest, 2005, 115: 739-746.
Hartmann, et al., Identification and functional analysis of tumor-infiltrating plasmacytoid dendritic cells in head and neck cancer, Cancer Res, 2003, 63: 6478-6487.
Friedberg et al., Combination immunotherapy with a CPG oligonucleotide(1018 ISS) and rituximab in patients with non-Hodgkin lymphoma: increased interferon-$\alpha/\beta$-inducible gene expression, without significant toxicity, Blood, 2005, 105: 489-495.
Senti et al., Use of A-type CpG oligodeoxynucleotides as an adjuvant in allergen-specific immunotherapy in humans: a phase I/IIa clinical trial, Clinic Experim Allergy, 2009, 39(4): 562-570.
Carpentier et al., Phase 1 trial of a CpG oligodeoxynucleotide for patients with recurrent glioblastoma, Neuro-Oncol, 2006, 8(1): 60-66.
Pashenkov et al., Phase II trial of a toll-like receptor 9-activating oligonucleotide in patients with metastatic melanoma, Journal of Clinical Oncology, 2006, 24(36): 5716-5724.
Van Ojik, et al., Phase I/II study with CpG 7909 as adjuvant to vaccination with MAGE-3 protein in patients with MAGE-3 positive tumors, Ann Oncol, 2002, 13.suppl 5:157-158.
International Search Report of PCT/CN2021/084467, Jul. 6, 2021.
Office Action in Japanese Patent Application No. 2022-559536; mailed Mar. 6, 2025.
Yang et al: “CpG oligodeoxynucleotides with double stem-loops show strong immunostimulatory activity”. International Immunopharmacology, vol. 15, No. 1,Nov. 7, 2012 (Nov. 7, 2012), pp. 89-96.
Wang et al: “A CpG oligodeoxynucleotide acts as a potent adjuvant for inactivated rabies virus vaccine”, Vaccine, Elsevier, Amsterdam, NL, vol. 26, No. 15, Feb. 13, 2008 (Feb. 13, 2008), pp. 1893-1901.
Extended European Search Report and Written Opinion in European Patent Application 21778756.3, mailed Aug. 30, 2024.

* cited by examiner

Fig. 5 (continue)

CpG ODN HAVING IMMUNOREGULATORY FUNCTION AND USE THEREOF

FIELD OF THE INVENTION

The present invention relates to a CpG ODN having immunoregulatory function and use thereof. The CpG ODN has good immunostimulatory activity, can stimulate the proliferation of B cells, and produce cytokines. It can be used as a vaccine adjuvant either alone or in combination with other adjuvants to exert a synergistic effect, and can also be used in the preparation of drugs for preventing or treating tumors, infections and allergies.

BACKGROUND OF THE INVENTION

In 1984, it was found that the nucleic acid component of Bacille Calmette-Guérin (BCG) has antitumor effects in a mouse tumor-bearing model, and it was successfully applied to the treatment of human tumors (Tokunaga T, Yamamoto H, Shimada S, et al. Antitumor activity of deoxyribonucleic acid fraction from *Mycobacterium bovis* BCG. I. Isolation, physicochemical characterization, and antitumor activity. J Natl Cancer Inst, 1984, 72(4):955-962). After degradation analysis with ribonuclease and deoxyribonuclease, it was proved that the component that really works was the deoxyribonucleic acid in the bacteria (Tokunaga T, Yamamoto S, Namba K. A synthetic single stranded DNA, Poly(dG, dC), induces interferon-alpha/beta and gamma, augments natural killer activity, and suppresses tumor growth. Jpn J Cancer Res, 1988, 79(6): 682-686; Tokunaga T, Yano O, Kuramoto E, et al. Synthetic oligonucleotides with particular base sequences from the cDNA encoding proteins of *Mycobacterium bovis* BCG induce interferon and activate natural killer cells. Microbiol Immunol, 1992, 36(1): 55-66). Sequence analysis showed that the oligodeoxynucleotide (ODN) with immune activity contained at least one or more CG dinucleotides in the sequence, wherein the CGs were linked by phosphorus (p). Therefore, oligodeoxynucleotides (ODN) were collectively referred to as a CpG oligodeoxynucleotides (CpG ODN), also known as immune activating sequences (ISS).

The immunostimulatory activities of CpG ODNs are affected by the structures themselves. In the genomes of pathogenic microorganisms such as bacteria, there are many CG dinucleotides. However, in human and vertebrate genomes, CG dinucleotides are rarely found, and even if there are CG dinucleotides in human and vertebrate genomes, cytosine and guanine nucleotides therein are usually methylated. Deletion, reversion and cytosine methylation of CpG dinucleotides may lead to loss of their activity, indicating that the presence of unmethylated CpG dinucleotides in CpG ODNs is the basis for the immunostimulatory activity (Ling Shigan. Research Progress of Immunoreactive Oligodeoxynucleotide CpG[J]. Chinese Journal of Microbiology and Immunology, 2008, 28(6): 571-576). In CpG ODNs, multiple deoxynucleotides are regularly arranged with various combinations. However, the immune activity of CpG ODNs with different sequence structures varies significantly, and alterations of one or several nucleotides in the sequence may greatly affect the immune activity thereof. Therefore, understanding and mastering the relationship between structure and activity will help us to design more sequences with immune activities.

For the CpG ODN with the activity of stimulating B lymphocytes in mice, the base sequence thereof generally has the following rules: the two bases near the 5' end of CpG dinucleotides are generally purines, preferably GpA, and the two bases near the 3' end of CpG dinucleotides are generally pyrimidines, preferably TpC or TpT (Krieg A M, Yi A K, Matson S, et al. CpG motifs in bacterial DNA trigger direct B-cell activation [J]. Nature, 1995, 374(6522):546-549). The C or G near the 5' end of CpG dinucleotide may significantly inhibit the activity of CpG ODN in stimulating NK lymphocytes in mice, whereas the C near the 3' end has little effect on the activity. It can be seen that GACGTT/C with GA at the 5' end is a CpG motif that has a strong effect on mice, whereas the immune activity of GCCGTT/C or GGCGTT/C motif obtained by replacing the GA at the 5' end with GC or GG is reduced. Human peripheral blood mononuclear cells can be activated by motifs containing "GTCGTT", "TTCGTT", or "AACGTT", wherein the most active motif is GTCGTT (Ballas Z K, Rasmussen W L, Krieg A M. Induction of NK activity in murine and human cells by CpG motifs in oligodeoxynucleotides and bacterial DNA [J]. J Immunol, 1996, 157(5): 1840-1845). Multiple TCG repeats help to enhance the stimulatory effect of CpG ODN on human B cells and NK cells (Hartmann G, Krieg A M. Mechanism and function of a newly identified CpG DNA motif in human primary B cells [J]. J Immunol, 2000, 164(2):944-953). T7 and T8 containing multiple TCG repeats also have a good immunostimulatory activity on human PBMCs. Multiple TCG repeats form the GTCGTC motif, indicating that the GTCGTC motif formed when the 3' end of the CpG dinucleotide is TpC also has a strong immunostimulatory activity on humans (Xu Honglin, Wang Siqing, Wang Shifeng. Delineation of CpG motifs for activating human immune cells [J]. Chinese Journal of Microbiology and Immunology, 2001, 21(5): 471-475). There are two or more copies of 5'-NTCGTT-3' motif in the CpG ODN sequence, with a length of 15-35 nucleotides, wherein the N does not represent A or G. Such CpG ODN has a good immunostimulatory activity on human and mouse immune cells in vitro (Xu Honglin. Phosphorothiolated oligodeoxynucleotides with immunostimulatory activity and uses thereof, CN 101492672 A). The core sequence of CpG ODN is a 6-nucleotide motif with a general formula of 5'-X1-X2-CG-Y1-Y2-3', wherein X1 is a purine base nucleotide, X2 is also a purine or thymine (T), and Y1 and Y2 both are pyrimidines. Furthermore, in addition to said 6-nucleotide motif, surrounding sequences and sequences between multiple CpGs also have an effect on the activity of CpG ODNs (Krieg A M, Hartmann G, Yi A K. Mechanism of action of CpG DNA. Curt Top Microbiol, 2000. 247(1):1-21). Other studies have found that the arrangement of bases adjacent to the two flanks of CpG mostly follows the following rules: 5'PurPurCGPyrPyr 3', that is, two purines at the 5' end and two pyrimidines at the 3' end (G. Mutwiri, R. Pontarollo, S. BaBIUK. Biological activity of immunostimulatory CpG ODN motif in domestic animals. Veterinary Immunopathology, 2003, 91: 89-103).

TLR 9 is a member of the Toll-like receptors (TLRs) family, which mainly recognizes CpG motifs in bacterial DNA. CpG ODN can stimulate the innate immune response of an individual in a TLR9-dependent manner. CpG ODNs in viral and bacterial genomes are natural agonists of TLR9. Therefore, TLR9 initiates a Th1-dominant immune response once the cells are infected with bacteria or the bacteria are ingested into the cells (AHLERS J D, BELYAKOV I M. Memories that last forever: Strategies for optimizing vaccine T-cell memory [J] Blood, 2010, 115(9); 1678-1689).

CpG ODN not only stimulates cells expressing TLR 9 molecules, triggers an immune regulatory cascade, and ultimately produces pro-inflammatory cytokines and chemokines, but also improves the antigen-presenting function of dendritic cells, monocytes and macrophages, induces the proliferation of B cells, stimulates the immune protection activity of NK cells, and induces immune responses in the body. Therefore, the CpG ODN is an immune adjuvant with high efficacy and low toxicity, and is of great value in the treatment of diseases (SUN S Q, ZHANG X H, TOUGH D F. Type I interferon-mediated stimulation of T cells by CpG DNA [J] J. Exp Med, 1998, 188(12): 2335-2342).

The vaccine adjuvant activity of CpG ODN has been validated in numerous animal experiments for preventive and therapeutic vaccines. In mouse models, CpG ODN is used in combination with various vaccines such as vaccines against papilloma virus, hepatitis B virus, *Brucella, Chlamydia*, HIV, *Aspergillus*, mycobacteria, trypanosomes, Bursal disease virus, hepatitis C virus, cytomegalovirus, dengue virus, rabies virus, influenza virus and the like. Since 2000, more than 20 vaccines with the CpG ODN as an adjuvant have been clinically studied. (KRIEG A M. Therapeutic potential of Toll-like receptor 9 activation [J]. Nat Rev Drug Discov, 2006, 5(6): 471-484; Dennis M Klinman. CpG DNA as a vaccine adjuvant [J]. Expert Rev Vaccines, 2003, 2(2): 305-315; KRIEG A M. CpG still rocks! Update on an accidental drug [J]. Nucleic Acid Ther. 2012, 22(2): 77-89). B-type CpG ODN is the main research object of the experiment, which is used as a vaccine adjuvant for the prevention and treatment of infectious diseases. A HEPLISAV-B hepatitis B vaccine by Dynavax has been approved by the FDA in November 2017.

The inhibitory effect of CpG ODN on viruses has been confirmed in experiments on respiratory syncytial virus, hepatitis virus, HIV, etc. (Liu S, Sun W, Cao Y. Study on anti-HBV effects by antisense oligodeoxynucleotides in vitro. China Journal of Preventive Medicine, 2001, 35 (5), 338-340; Lund O S, Hansen J E. Inhibition of HIV-1 replication by chimeric phosphorothioate oligodeoxynucleotides applied in free solution. Intervirology, 1998, 41 (2-3), 63-68).

CpG ODN has an antitumor activity in many mouse models, and in the case of relatively small tumors, CpG ODN alone can effectively induce T cell-mediated tumor rejection response. However, for larger tumors, the CpG ODN is required to be combined with other treatments such as monoclonal antibody, radiotherapy, surgery, and chemotherapy, and will have a strong synergistic effect. The CpG ODN-mediated tumor regression can be T cell-dependent and NK cell independent, or NK cell dependent and T cell independent. As an adjuvant for melanoma polypeptide antigen vaccine, CpG 7909 can significantly improve the survival of patients bearing tumors, and can induce a strong melanoma protein antigen-specific CD8+ T cell response (van Ojik, H. et al Phase I/II study with CPG 7909 as adjuvant to vaccination with MAGA-3 Protein in Patients with MAGA-3 Positive tumors. Ann Oncol 2005, 13, 157; Speiser, D. E. et al. Rapid and strong human CD8(+) T cell responses to vaccination with peptide, IFA, and CPG oligodeoxynucleotide 7909. J Clin Invest, 2005, 115, 739-746).

CpG ODN alone or in combination with anti-tumor antibodies can both induce Th1 cytokine secretion and enhance ADCC effect (Hartmann, E. et al. Identification and functional analysis of tumor-infiltrating plasmacytoid dendritic cells in head and neck cancer. Cancer Res 2003: 63, 6478-6487). The combination of B-type 1018 ISS and rituximab has a good efficacy in the treatment of non-Hodgkin's lymphoma and has entered clinical trials (Friedberg, J. W. et al. Combination immunotherapy with a CPG oligonucleotide (1018 ISS) and rituximab in Patients with non-Hodgkin lymphoma: increased interferon-GO-inducible gene expression, without significant toxicity. Blood 2005: 105, 489-495).

In clinical trials, the proliferation and metastasis of cancer cells were inhibited to a certain extent in some patients with recurrent glioblastoma subjected to a radiotherapy after injection of CpG ODN around the tumor (Senti G, Johansen P, Haug S, et al. Use of A-type CpG oligodeoxynucleotides as an adjuvant in allergen-specific immunotherapy in humans: a phase I/IIa clinical trial[J]. Clinic Experim Allergy, 2009, 39(4): 562-570; Carpentier A, Laigle-Donadey F, Zohar S, et al. Phase 1 trial of a CpG oligodeoxynucleotide for patients with recurrent glioblastoma [J]. Neuro-Oncol, 2006, 8(1): 60-66). Other clinical trials showed that intratumoral injection of CpG 7909 achieved complete regression of melanoma tumors, but 5 patients with metastatic melanoma failed to prevent tumors at distant sites (Pashenkov M, Goess G, Wagner C, et al. Phase II trial of a toll-like receptor 9-activating oligonucleotide in patients with metastatic melanoma [J]. Clinical Oncol Official J American Society Clinic Oncol, 2006. 24(36):5716-5724). Data from two Phase 3 clinical trials of CpG 7909 showed that it failed to improve clinical outcomes as compared to chemotherapy alone. There remains a continuing need in the art to discover new immunomodulatory polynucleotides.

CpG ODN is an immune adjuvant with high efficacy and low toxicity, and is of great potential value in the treatment of infectious diseases, immunodeficiency diseases, tumors, and allergic diseases. However, the current practical application is limited, and more in-depth researches are needed to design more effective sequence structures, so that they can exert their potential more widely and can be used in clinics more safely and efficiently.

SUMMARY OF THE INVENTION

The present invention provides a series of CpG ODNs with immunoregulatory function. The structure of these CpG ODNs is novel, and they have immunostimulatory effects on both mice and humans, and thus are of great clinical value. Specifically, the present invention solves the problems in the art through the following technical solutions:

1. An immunoregulatory CpG ODN comprising or consisting of a nucleotide sequence selected from SEQ ID NO: 1-6, wherein at least one nucleotide in the nucleotide sequence is a chemically modified nucleotide having a structure shown in general formula I:

(I)

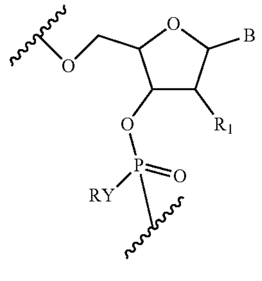

wherein, Y is S or O, R is H or a positively charged counterion, B is independently an unmodified or modified nucleobase, and R1 is H, F, Cl, OH, OMe, Me, or O-ethyloxymethyl.

2. The immunoregulatory CpG ODN of item 1, wherein Y is S.
3. The immunoregulatory CpG ODN of item 1 or 2, wherein all nucleotides in the nucleotide sequence of the CpG ODN are chemically modified nucleotides having the structure shown in general formula I.
4. The immunoregulatory CpG ODN of item 3, wherein the sequence of immunoregulatory CpG ODN is selected from SEQ ID NOs: 1-6, preferably completely-phosphorothioated SEQ ID NOs: 1-6, more preferably completely-phosphorothioated SEQ ID NO: 3 or 6.
5. A pharmaceutical composition comprising the immunoregulatory CpG ODN of any one of items 1 to 4 and a pharmaceutically acceptable carrier.
6. Use of the immunoregulatory CpG ODN of any one of items 1 to 4 in the preparation of a vaccine adjuvant.
7. The use of item 6, wherein the vaccine is a rabies vaccine, preferably, the amount of CpG ODN is 0.01 μg-1000 μg/ml, more preferably 1-10 μg/ml, for example, 1, 3, or 10 μg/ml.
8. The use of item 6, wherein the vaccine is a SARS-COV-2 vaccine, preferably a SARS-COV-2 inactivated vaccine, and the amount of CpG ODN is 0.01 μg-1000 μg/ml.
9. The use of any one of items 6-8, wherein the vaccine adjuvant further comprises one or more other adjuvants that work together with the immunoregulatory CpG ODN, such as insoluble aluminum salt colloids, oil-water emulsions, microorganisms and metabolites, nucleic acids and the analogs thereof, cytokines, immunostimulatory complexes, propolis, and liposomes.
10. Use of the immunoregulatory CpG ODN of any one of items 1 to 4 or the pharmaceutical composition of item 5 in the preparation of a medicament for the prevention or treatment of tumors, microbial infections or allergies in a subject.
11. The use of item 10, wherein the subject is a human or an animal, such as a mouse, rat, domestic animal, such as a dog, pig, cattle, horse; a domestic bird, such as chicken, duck, and goose.
12. A vaccine comprising the immunoregulatory CpG ODN of any one of items 1~4 and an antigen, wherein the antigen is a rabies antigen or a SARS-COV-2 antigen.
13. The vaccine of item 12, wherein the vaccine is a vaccine for a human or an animal, and the immunoregulatory CpG ODN is an immunoregulatory CpG ODN represented by completely-phosphorothioated SEQ ID NO: 3, and the amount of CpG ODN is 0.01 μg-1000 μg/ml, more preferably 1-10 μg/ml, such as 1, 3, or 10 μg/ml.
14. The vaccine of item 12, wherein the vaccine is a SARS-COV-2 vaccine, preferably a SARS-COV-2 inactivated vaccine, wherein the vaccine further comprises an aluminum adjuvant, such as aluminum hydroxide adjuvant.
15. The vaccine of item 14, wherein the immunoregulatory CpG ODN is an immunoregulatory CpG ODN represented by completely-phosphorothioated SEQ ID NO: 6.
16. The vaccine of item 15, wherein the content of the antigen is 1-10 μg/mL, such as 2, 4 or 8 μg/mL; the content of the aluminum hydroxide is 1-1000 μg/mL, preferably 300-500 μg/mL mL; the content of the immunoregulatory CpG ODN is 1-1000 μg/mL, preferably 2-500 μg/mL, such as 5 μg/mL, 20 μg/mL, 40 μg/mL, 80 μg/mL, or 400 μg/mL.

DEFINITIONS

CpG ODN

Figure 1:
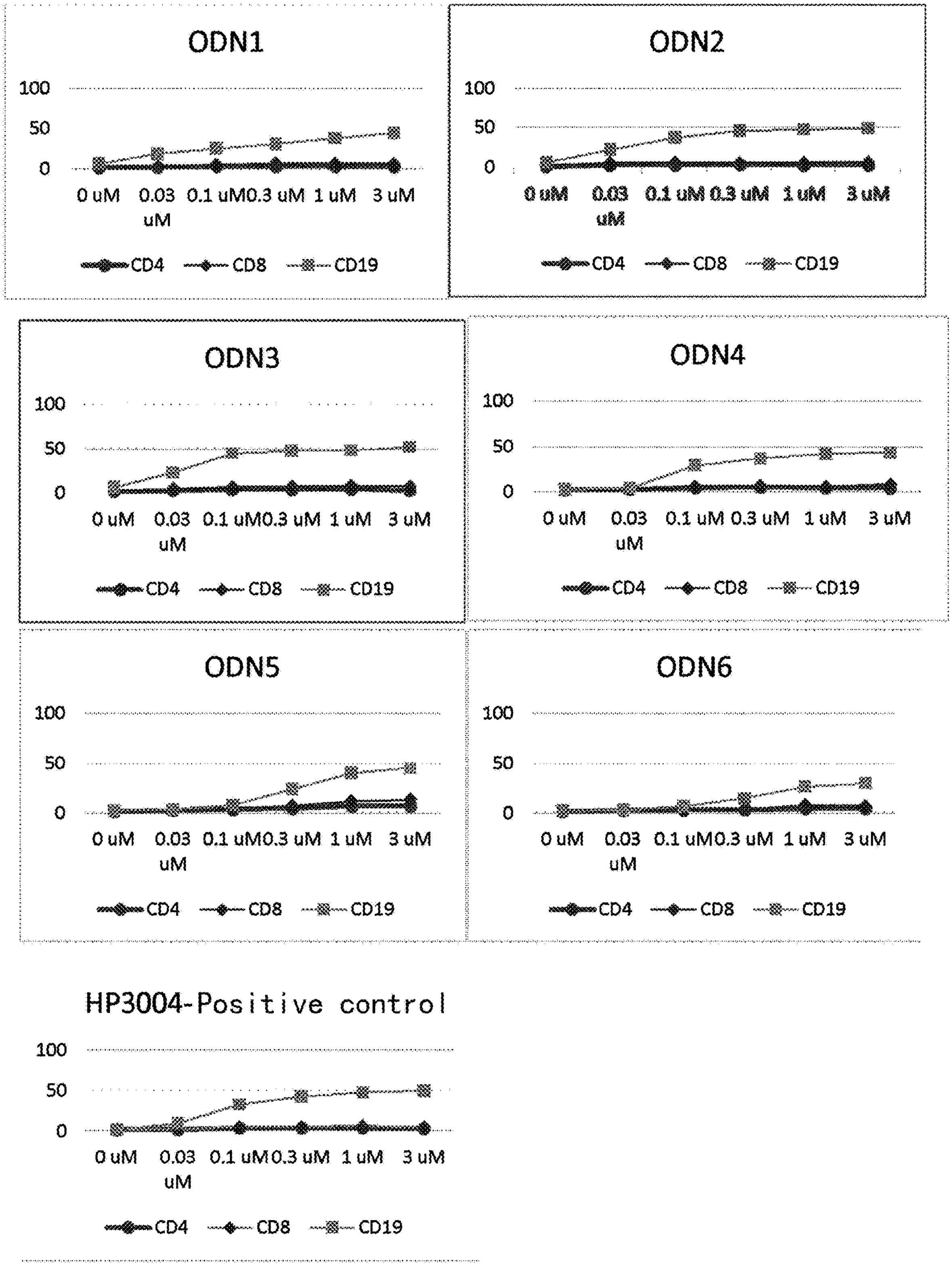
FIG. 1 shows the effect of CpG ODN on the proliferation of mouse spleen T and B cells.

The CpG ODNs in the present invention are unmethylated dinucleotides linked by phosphodiester bonds, and have immunostimulatory effects. The CpG ODN can promote the proliferation and differentiation of B cell and the secretion of IL-6, thereby inducing the secretion of antibodies; activating presenting cells such as monocytes, macrophages and dendritic cells to secrete various cytokines (for example, IL-12, IL-6, TNF-α, IFN-α and IFN-β, etc.). The cytokines indirectly promote the activity of killer T cells (CTLs) and natural killer cells (NK cells), induce cellular immunity by intracellular pathogens, and induce the secretion of IFN-γ by NK cells and T cells. In addition to the induction of innate immune response, CpG ODNs can also potentiate antigen-specific responses for the following reasons: (1) there is a strong synergy between the signaling pathways initiated by B-cell antigen receptors and the B cell signaling pathway initiated by CpG; (2) the CpG ODNs can increase antigen-specific T helper Th1-like cytokines, thereby enhancing antigen-specific responses of B cells and T cells, and (3) cellular responses require positive regulation by costimulatory molecules.

As early as the 1890s, it was found that injecting bacterial extracts into cancer patients could significantly relieve the disease. Later studies showed that bacterial DNA had direct immune-stimulating and anti-tumor effects. Through experimental research on synthetic oligodeoxynucleotides, it was found that the immunostimulatory effect of bacterial DNA is related to unmethylated CpG dinucleotides therein.

The CpG ODN with immunostimulatory activity has the following basic structural features:

a. CpG motif is the basic structure of CpG ODN to produce immunostimulatory effect, and is composed of CpG dinucleotide and two bases each at 5' end and 3' end thereof.

b. The purines and pyrimidines on both flanks of CpG and the spacing between CpGs can affect the immunostimulatory activity of CpG ODN and the characteristics of effect.

c. Regarding the number of CpG motifs contained in the ODN, 2-4 CpG motifs are generally optimal, and the spacing between CpG motifs is usually at least two bases (preferably thymines).

d. CpG ODNs containing poly-G sequences (composed of 3 or more guanines) have a strong effect on stimulating plasmacytoid dendritic cells (pDCs) to produce interferon-a; completely thio-modified CpG ODNs are the most stable with the best stimulation effect on B cells, but the effect of completely thio-modified CpG ODNs in stimulating pDC to produce IFN-α is weaker than that of partially thio-modified CpG ODNs.

Based on functional characteristics, CpG ODNs can be classified into three types (Tomoki Ito, et al., Blood, 2006, Vol 107, Num 6:2423-2431):

(1) A-Type CpG ODN, which is synthesized by a chimeric backbone, wherein the 5' and 3' ends of the backbone are phosphorothioate and the middle CpG region is a phosphodiester; these ODNs can activate natural killer cells (NK cells) and plasmacytoid dendritic cells (pDC cells) well to produce large amounts of IFN-α but can only activate B cells to a limited extent;

(2) B-type CpG ODN, which is synthesized via a nuclease-resistant phosphorothioate backbone, can well activate B cells and pDC cells to produce IL-12 and induce antibody secretion, but can only activate NK cells to a limited extent; the B-type CpG ODN is generally effective as a vaccine adjuvant; and (3) C-type CpG ODN, which is synthesized through a phosphorothioate backbone, has a stimulatory activity between that of A-type and B-type CpG ODNs, for example, it can well activate B cells, but also well activate NK cells and pDC cells.

The immunoregulatory CpG ODN used in the present invention comprises or consists of a nucleotide sequence selected from SEQ ID NO: 1-6, wherein at least one nucleotide in the nucleotide sequence is a chemically modified nucleotide having a structure shown in general formula I:

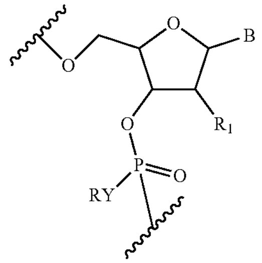

(I)

wherein, Y is S or O, particularly S; R is H or a positively charged counterion; B is independently an unmodified or modified nucleobase; and $R_1$ is H, F, Cl, OH, OMe, Me, O-ethyloxymethyl. The Me herein represents a methyl.

The bases in the CpG ODNs of the present invention may be unmodified, or partially modified, or completely modified nucleobases (wherein, natural nucleobases include adenine, guanine, cytosine and thymine). Modification of the CpG ODN backbone may include partially or completely phosphorothioated modification of the bases in the CpG ODNs of the present invention. The modification can be made during the synthesis of the oligonucleotide or after synthesis, and the modification can occur on phosphodiester bridges between nucleosides, on ribose units and/or on natural nucleobases (i.e., adenine, guanine, cytosine, and thymine). When modifications are made during the synthesis of the oligonucleotide, the modified base can be incorporated into the oligonucleotide or at the end of the oligonucleotide. When modifications are made after synthesis of the oligonucleotide, the modification can be carried out by using reactive groups, for example, by amino-modifying moieties, by 3' or 5' hydroxyl groups, or by phosphate groups.

The chemical modification in the present invention may include modification of backbone in the CpG ODN of the present invention, including but not limited to, modification of the backbone by phosphorothioate to obtain a phosphorothioated backbone, which is a stable sugar phosphate backbone of a nucleic acid molecule in which sulfur substitutes the oxygen of an unbridged phosphate on at least one internucleotide linkage, or, sulfur substitutes the oxygen of the unbridged phosphate on every or every other internucleotide linkage. Other modifications to the oligonucleotide backbone can also be made, for example, the oligonucleotide backbone can be modified by using non-ionic DNA analogs, such as alkyl phosphates and aryl phosphates, wherein, the oxygen in charged phosphates is substituted with alkyl or aryl groups, or the backbone is modified with phosphodiester and alkyl phosphotriester, wherein the charged oxygen is alkylated.

The immunoregulatory CpG ODN of the present invention has a novel sequence structure, and it has immunostimulatory effects on both mice and humans, and thus is of great clinical value.

In a particular embodiment, the sequence of the immunoregulatory CpG ODN of the present invention is ODN3 or ODN6, which comprises at least one chemically modified nucleotide having a structure shown in general formula I, wherein the substituent groups in general formula I are as defined above.

In one embodiment, the present invention also provides a pharmaceutical composition comprising the immunoregulatory CpG ODN described herein and a pharmaceutically acceptable carrier. "Pharmaceutically acceptable carrier"

refers to ingredients other than the active ingredient in a pharmaceutical formulation that are non-toxic to a subject. Pharmaceutically acceptable carriers include, but are not limited to, buffers, excipients, stabilizers or preservatives.

Subject

The term "subject" as used herein refers to animals including, but not limited to, primates (e.g., humans), cattle, sheep, goats, horses, dogs, pigs, cats, rabbits, rats, mice, fish, birds, such as domestic birds, such as chickens, ducks, geese, and the like. Preferably, the animal is a mammal. In a preferred embodiment, the subject is a human.

Immune Cells

Immune cells in the present invention refer to all cells involved in and associated with immune responses and precursor cells thereof. Immune cells include T cells (such as CD4+ cells, CD8+ cells and various other T cell subtypes), B cells (such as CD19), natural killer cells (NK cells), macrophages, monocytes, dendritic cells and neutrophils.

Specific T lymphocytes and specific B lymphocytes expressing specific antigen receptors are involved in mediating adaptive immune responses. After antigen-specific stimulation, B lymphocytes can activate, proliferate and differentiate into plasma cells, produce specific antibodies, and mediate humoral immune responses. After antigen-specific stimulation, T lymphocytes can activate, proliferate and differentiate into effector T cells, mediate cellular immune responses and assist humoral immune responses. In addition, in the initiation stage of the adaptive immune response, professional APCs such as dendritic cells and mononuclear macrophages are involved to present antigens to activate T cells. In the effector stage of the adaptive immune response, mononuclear macrophages, NK cells and the like are involved to be cooperated with T cells, antibodies, etc. to play a role of removing antigens.

The cells involved in an innate immune response mainly include mononuclear macrophages, granulocytes, dendritic cells, NK cells, endothelial cells, mast cells, erythrocytes, platelets, etc., as well as a small number of T and B lymphocyte subgroups. NK cells are a third type of lymphocytes, which have a non-specific cytotoxic activity and play an important role in the innate immune response against viral infections and tumors. Mononuclear macrophages, granulocytes, etc. have strong phagocytosis and killing functions, and participate in inflammatory responses by releasing a large number of active products.

The synergistic effect of the antigen and CpG ODN(s) of the present invention induces both humoral immune response and cellular immune response, strengthens the immune function of Th1 type T cells, and greatly enhances the immune response of T cells.

Vaccine

The "vaccine" in the present invention is a vaccine well known to those skilled in the art, and generally refers to any biological preparation that can induce the production of specific antibody and/or cellular immunity against a specific pathogen in an individual after inoculation by injection or mucosal route, thereby conferring protection or ability of eliminating the pathogen to the individual, and include proteins, polysaccharides, nucleic acids, living vectors or infectious agents, etc. Vaccines are autoimmune preparations for the prevention of infectious diseases, which are prepared from pathogenic microorganisms (such as bacteria, rickettsia, viruses, etc.) and metabolites thereof by artificially attenuating, inactivating or genetic engineering and other methods. Vaccines retain the properties of a pathogen in stimulating the immune system of an animal body. When the animal is exposed to such an innocuous pathogen, the immune system will produce some protective substances, such as immune hormones, active physiological substances, special antibodies, etc.; when the animal is exposed to such a pathogen again, the immune system of the animal will follow its original memory and produce more protective substances to prevent the damage of the pathogen.

A "vaccine" as used herein refers to a formulation designed to induce an immune response against an antigen. The vaccine may be therapeutic, which is administered during treatment to boost the immune response or drive a response in a particular direction; or may be prophylactic, which is administered before or shortly after developing a disease. The vaccine may be both therapeutic and prophylactic at the same time in treating disease that has developed and preventing disease that will recur in the future. The vaccine can be administered to a subject by conventional administration methods in the art. As used herein, the term "administration" or "administering" includes all suitable means of providing a substance to a patient. Conventional routes include administration by oral, sublingual, transmucosal, transdermal, rectal, vaginal, subcutaneous, intramuscular, intravenous, intraarterial, intrathecal, administration via catheters, and administration via implants, etc.

The antigen of the present invention can be used to prepare a medicament for inducing an immune response against the antigen in a subject. In one embodiment, the antigen of the present invention can be used to prepare a rabies vaccine. In a preferred embodiment of the present invention, the antigen of the present invention can be used to prepare a rabies vaccine for animals and humans. The rabies vaccines for animals include inactivated vaccines, attenuated vaccines and genetically engineered vaccines. The rabies vaccines for humans include neural tissue-derived vaccines, avian embryo-cultured vaccines, cell-cultured vaccines, subunit and refined vaccines, and genetically engineered vaccines. In one embodiment, the antigen of the present invention can be used to prepare a SARS-COV-2 vaccine.

Vaccine Adjuvant

"Vaccine adjuvants" or "adjuvants" in the present invention refer to vaccine adjuvants well known to those skilled in the art. The word "adjuvant" originates from the Latin "Aduvare", which means assistance or enhancement. The vaccine adjuvant is an additive to vaccine. It can enhance the immune response to an antigen or change the type of immune response when it is injected into the body prior to the antigen injection or after mixed with the antigen, and it is a non-specific immunopotentiator, and has no antigenicity itself.

At present, there is no uniform standard for the classification of adjuvants in the world. Commonly used adjuvants mainly include insoluble aluminum salt colloids, oil-water emulsions, microorganisms and their metabolites, nucleic acids and analogs thereof, cytokines, immune stimulating complexes, propolis, liposomes, etc. The immunoregulatory CpG ODN(s) of the present invention can also be used as a vaccine adjuvant, and can exert an excellent adjuvant function. The immunoregulatory CpG ODN(s) of the present invention can be used alone as an adjuvant for a vaccine (such as a rabies vaccine or a SARS-COV-2 vaccine), or be used in combination with other commonly used adjuvants as adjuvants for a vaccine (such as a rabies vaccine or a SARS-COV-2 vaccine). The immunoregulatory CpG ODNs and these commonly used adjuvants can exert an additive effect or a synergistic effect to improve the immunogenicity of the antigen, thereby reducing the dose of the vaccine or improving the effect of the vaccine (such as reducing the dose of the vaccine or reducing the number of vaccine administration). Therefore, in one embodiment, the present invention also provides the use of the immunoregulatory CpG ODNs in the preparation of a vaccine adjuvant, preferably, the vaccine is a rabies vaccine or a SARS-COV-2 vaccine. In one embodiment, the vaccine adjuvant herein further comprises one or more other substances that synergistically function with the immunoregulatory CpG ODNs. When used as an adjuvant for a rabies vaccine or a SARS-COV-2 vaccine, the effective amount of the immunoregulatory CpG ODN(s) described herein can be determined by those skilled in the art through routine experiments, for example, the effective amount can be 0.01 μg-1000 μg/ml vaccine, including any number within the range of 0.01 μg-1000 μg/ml, e.g., 0.1 μg/ml, 0.2 μg/ml, 0.3 μg/ml, 0.4 μg/ml, 0.5 μg/ml, 0.6 μg/ml, 0.7 μg/ml, 0.8 μg/ml, 0.9 μg/ml, 1.0 μg/ml, 1.1 μg/ml, 1.2 μg/ml, 1.3 μg/ml, 1.4 μg/ml, 1.5 μg/ml, 1.6 μg/ml, 1.7 μg/ml, 1.8 μg/ml, 1.9 μg/ml, 2.0 μg/ml, 3.0 μg/ml, 4.0 μg/ml, 5.0 μg/ml, 6.0 μg/ml, 7.0 μg/ml, 8.0 μg/ml, 9.0 μg/ml, 10.0 μg/ml, 20.0 μg/ml, 30.0 μg/ml, 40.0 μg/ml, 50.0 μg/ml, 60.0 μg/ml, 70.0 μg/ml, 80.0 μg/ml, 90.0 μg/ml, 100.0 μg/ml, 200.0 μg/ml, 300.0 μg/ml, 400.0 μg/ml, 500.0 μg/ml, 600.0 μg/ml, 700.0 μg/ml, 800.0 μg/ml, 900.0 μg/ml, 1000.0 μg/ml vaccine.

Medicament

The term "medicament" or "pharmaceutical formulation" refers to a formulation in such a form that allows the biological activity of the active ingredient contained therein to be effective, and it does not contain additional components that are unacceptably toxic to the subject to which the formulation will be administered. In one embodiment, the present invention relates to use of the immunoregulatory CpG ODN(s) or the pharmaceutical composition in the preparation of a medicament for the prevention or treatment of tumors, microbial infections or allergies in a subject. The subject is a human or an animal, such as a mouse, a rat, a domestic animal, such as a dog, a pig, a cattle, a horse; a domestic bird, such as a chicken, a duck, and a goose. Those skilled in the art can determine the effective amount of the immunoregulatory CpG ODN(s) in the medicament or pharmaceutical formulation according to conventional methods, and determine the administration method of the medicament according to conventional methods.

DETAILED DESCRIPTION OF THE INVENTION

In order to make the purpose, technical solution, and advantage of the present invention more clear, the present invention will be further described in detail below with reference to specific Examples and Figures. The following Examples are only for the purpose of illustration, and the protection scope of the present invention shall be based on the appended claims.

EXAMPLES

Materials and Methods

All CpG ODNs were synthesized by Suzhou Ribo Life Science Co., Ltd, China, which include ODN 1 (5'-tcgcgacgttcgcgggacgttcccta-3', SEQ ID NO:1), ODN2(5'-tcgcgacgttcgcgcgacgttcgcta-3', SEQ ID NO:2), ODN3 (5'-tcgcgacgttcgccgacgttcgta-3', SEQ ID NO:3), ODN4 (5'-tggacgttcgtcgttcgtccttc-3', SEQ ID NO:4), ODN5 (5'-tcgtcgttcgtcgttcgacgttc-3', SEQ ID NO:5), ODN6 (5'-tcgaggttcgtcgttcctcgttc-3', SEQ ID NO:6) etc., wherein the ODN 1, ODN2, ODN3, ODN4, ODN5, ODN6 are all completely phosphorothioated sequences. HP3004 was a positive control CpG ODN (5'-tgactgtgaacgttcgagatga-3', SEQ ID NO:7, completely phosphorothioated), HP0000 was a negative control CpG ODN (5'-tggc-caagcttgggccccttgcaagggcc-3', SEQ ID NO:8, completely phosphorothioated). All CpG ODNs were dissolved in sterile/endotoxin-free water (InvivoGen, USA) and stored at −40° C. for use. The rabies vaccine was obtained from Changchun Biological Products Institute, China (Vero cell rabies vaccine)/Chengdu Kanghua Biological Products Co., Ltd., China (Human diploid cell rabies vaccine). The inactivated SARS-COV-2 vaccine was provided by Zhejiang Tianyuan biopharmaceutical Co., Ltd., China.

Human Peripheral Blood Concentrated Leukocytes and Experimental Animals:

Human peripheral blood concentrated leukocytes were purchased from Changchun Blood Station, China. Female BALB/c mice aged 6-8 weeks were purchased from Changchun Institute of Biological Products Co., Ltd., China.

Isolation and Culture of Human Peripheral Blood Mononuclear Cells (PBMCs):

The concentrated leukocytes from human peripheral blood were diluted with two volume of normal saline, and added to the surface of Ficoll separation solution (Corning, USA) in a plastic centrifuge tube by 1:1, and centrifuged at 2800 rpm for 20 min (8 increases and 0 decrease) to collect the suspension of mononuclear cell layer. The suspension was washed 3 times with 1×PBS, centrifuged at 1500 rpm for 5 min, the supernatant was discarded, and cells were suspended by RPMI-1640 (Corning, USA) complete medium added with 10% fetal bovine serum (Clark, USA), 1% penicillin/streptomycin (Hyclone, USA) and 1% HEPES (Invivogen, USA), plated in a 96-well U-shaped plate at $2\times10^5$ cells/well, and added with a CpG of different concentrations (0.03, 0.1, 0.3, 1 and 3 μM) respectively, and cultured in an incubator at 37° C., 5% $CO_2$.

Cytokine Secretion Assay:

Human PBMCs ($2\times10^5$ cells/well) and mouse spleen cells ($1\times10^6$ cells/well) were plated in 96-well U-shaped plates, and added with different concentrations of a CpG (0.03, 0.1, 0.3, 1, and 3 μM), respectively. After cultured in a 37° C., 5% $CO_2$ incubator for 16 h, the supernatant was collected, and then the levels of human IFN-α (Mabtech, Sweden), mouse IFN-α (eBioscience, Australia), mouse IL-6 (Mabtech, Sweden) and mouse TNF-α (Mabtech, Sweden) in the supernatant were detected according to the instructions of the ELISA kit.

Example 1. Preparation of CpG ODNs

The CpG ODNs were synthesized by an automated DNA synthesizer via a solid-phase phosphoramidite triester method by the steps of deprotection, activation, thiolation, and capping. The synthesized oligonucleotides were deprotected with concentrated ammonia, then purified and desalted. Purified oligonucleotides were lyophilized in sodium salt form and qualified by MS prior to use. Afterwards, CpG ODN sequences with a purity of >90% were obtained. The CpG ODNs indicated as ODN1, ODN2, ODN3, ODN4, ODN5 and ODN6 were used for subsequent experiments.

5'-DMT dA, dG, dC, dT and other phosphoramidite monomers were purchased from Shanghai Zhaowei Technology Development Co., Ltd. The corresponding supports were purchased from Chemgenes (Wilmington, MA).

2'-Substituted ribonucleoside phosphoramidites were purchased from Shanghai Zhaowei Technology Development Co., Ltd., Promega (Obispo, CA).

Example 2 the Effect of CpG ODNs on the Proliferation of Mouse Spleen T and B Cells Isolation and Culture of Mouse Spleen Cells:

The mouse spleen was isolated under sterile conditions, and the BALB/c mouse spleen cell suspension was prepared after grinding and filtration. The cells were suspended in RPMI-1640 complete medium, plated in 96-well U-shaped plates at $5\times10^5$ or $1\times10^6$ cells/well, added with different concentrations of a CpG (0.03, 0.1, 0.3, 1 and 3 μM) respectively, and cultured in a 37° C., 5% $CO_2$ incubator.

After cultured for 16 h, the cells were collected, washed twice with 1×PBS, and centrifuged at 1500 rpm for 5 min. The cells were resuspended with 1×PBS, and anti-CD4, anti-CD8 and anti-CD19 antibodies (BD, USA) were added into the cell suspension, and then incubated at 4° C. for 30 min in the dark. The cells were washed twice with 1×PBS, centrifuged at 1500 rpm for 5 min, resuspended in 1×PBS, and analyzed by flow cytometry using a BD LSRFortessa flow cytometer (BD, USA).

The supernatant was collected for ELISA analysis. The levels of CD4, CD8 and CD19 in the supernatant were measured by sandwich ELISA, and the effect of CpG ODNs on the proliferation of mouse spleen T and B cells was obtained. The results are shown in FIG. 1.

Conclusion: The CpG ODNs can greatly stimulate the activation of mouse spleen B cells (as shown by the level of CD19), induce the proliferation of mouse spleen B cells, and then upregulate the expression of costimulatory molecules and the secretion of cytokines (such as IL-6, TNF-α).

Example 3: Cytokine Induction in Mouse Splenocyte Cultures

Figure 2:
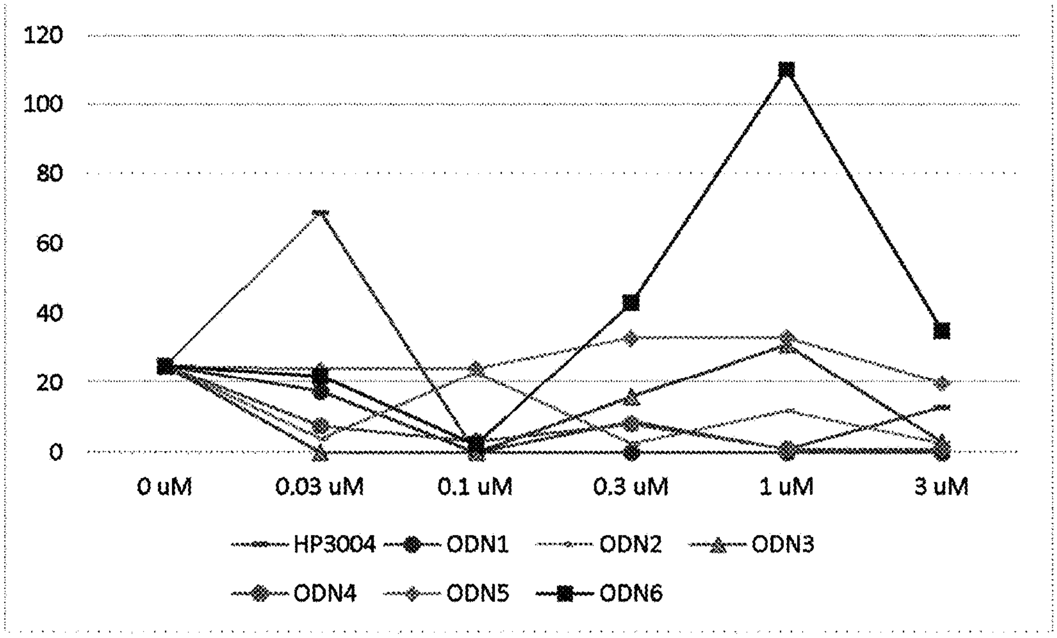
FIG. 2 shows the effect of CpG ODN in stimulating mouse splenocytes to produce cytokine IFN-α.
Figure 3:
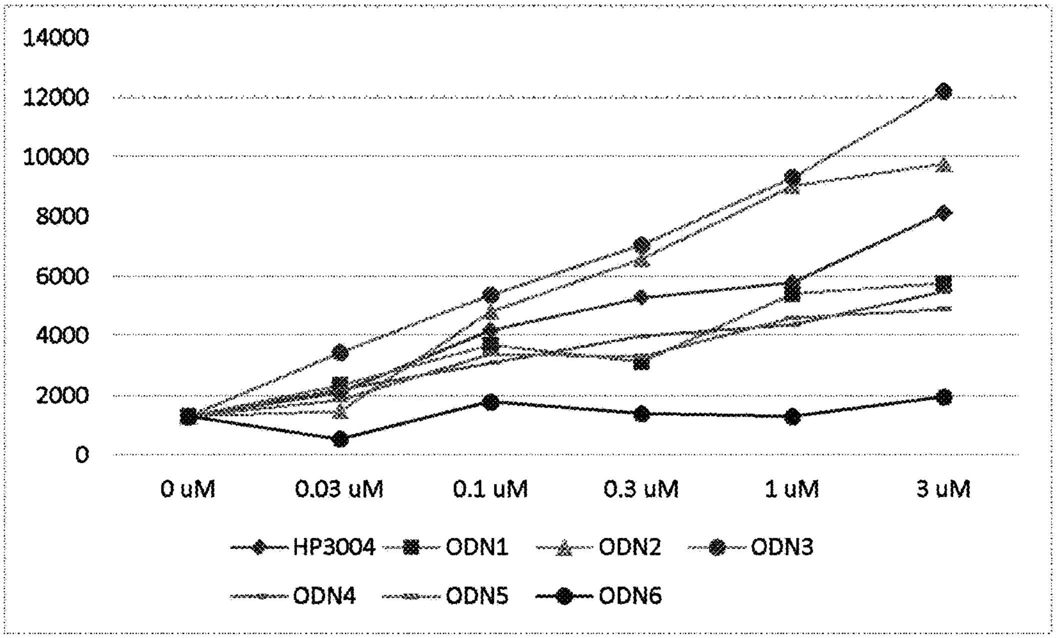
FIG. 3 shows the effect of CpG ODN in stimulating mouse splenocytes to produce cytokine IL-6.
Figure 4:
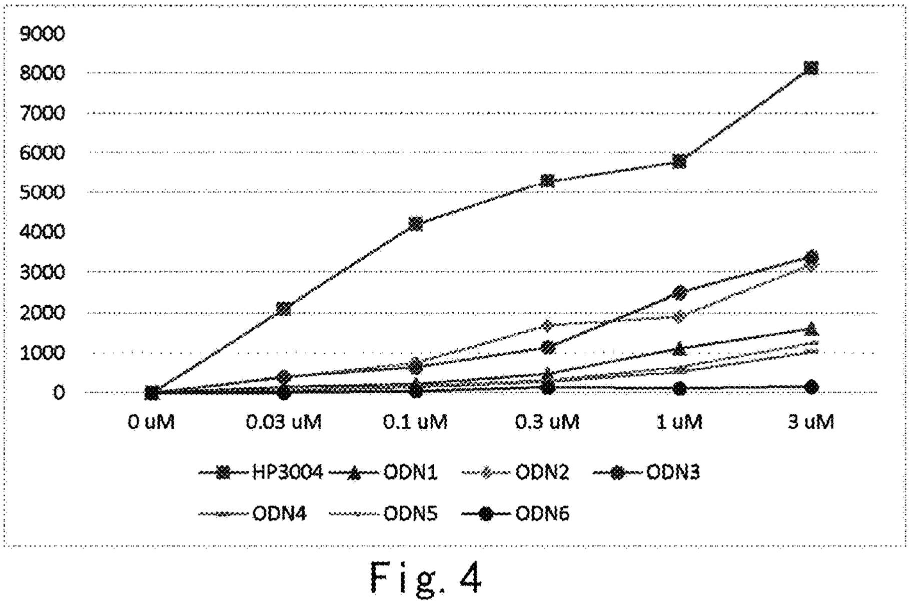
FIG. 4 shows the effect of CpG ODN in stimulating mouse splenocytes to produce cytokine TNF-α.

Splenocytes from 4-8 week old C57BL/6 mice were prepared and cultured in RPMI complete medium. Mouse splenocytes were inoculated in a 24-well petri dish at $5\times10^6$ cells/ml. CpG ODNs in PBS buffer were added to the cell culture to final concentrations of 0.03, 0.1, 0.3, 1 and 3 μM, respectively. The cells were then incubated at 37° C. for 24 h and the supernatant was collected for ELISA analysis. The levels of IFN-α, IL-6, and TNF-α in the supernatant were determined by sandwich ELISA. Reagents used in the Example including anti-cytokine antibodies and standards were purchased from BD PharMingen. The results were shown in FIGS. 2, 3, and 4. FIG. 2 shows that different CpG ODNs effectively stimulated secretion of IFN-α by pDC, wherein HP3004 was a positive control. FIG. 3 shows that different CpG ODNs stimulated secretion of IL-6 by B cells, in which HP3004 was a positive control. FIG. 4 shows that different CpG ODNs stimulated production of TNF-α by B cells, in which HP3004 was a positive control.

Conclusion: Different CpG ODN sequences up-regulated and stimulated the secretion of cytokines IL-6 and TNF-α.

Figure 5:
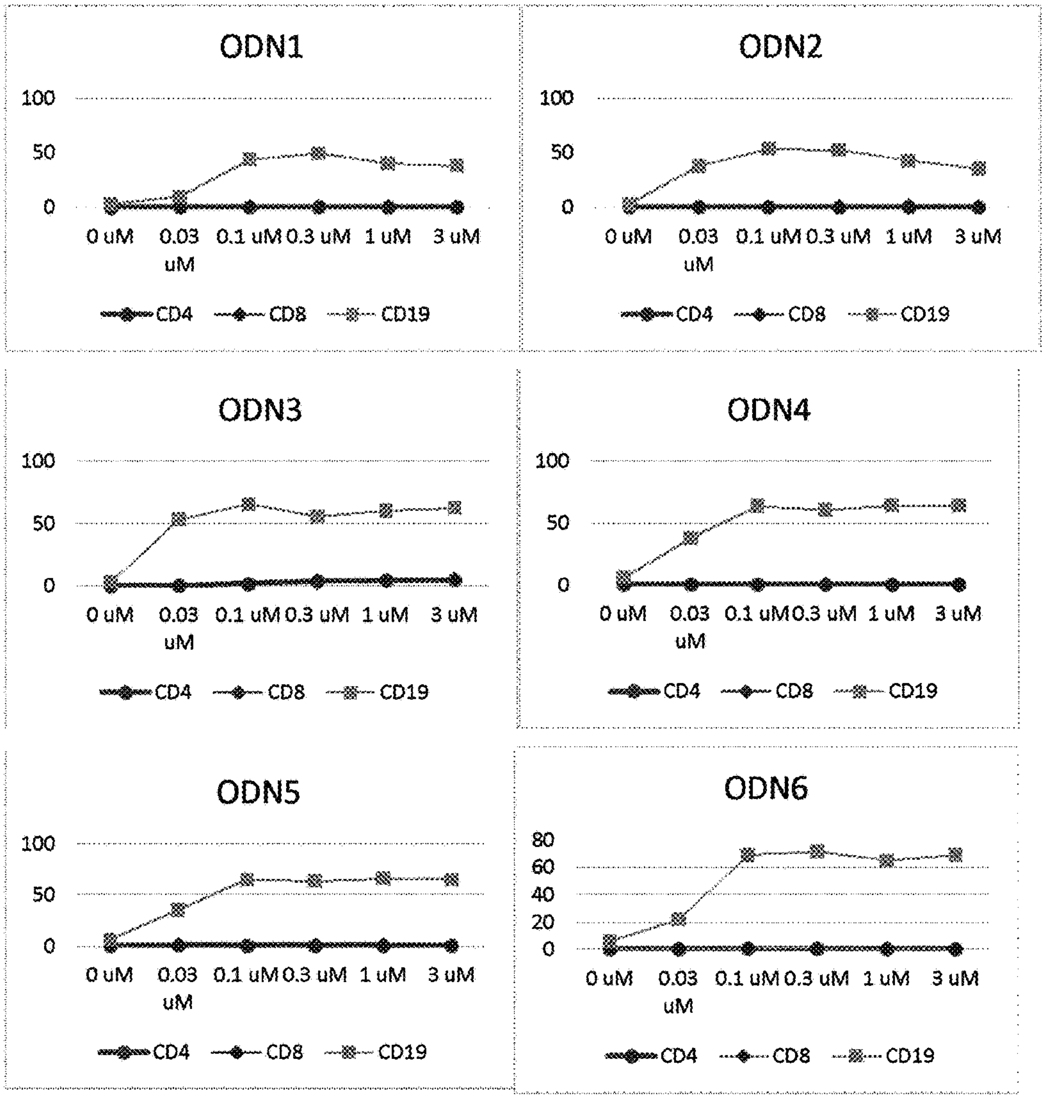
FIG. 5 shows the effect of CpG ODN on the proliferation of human PBMCs T and B cells.

Example 4 the Effect of CpG ODNs on the Proliferation of T and B Cells Induced by Human PBMC The medium used for analysis was RPMI1640 medium supplemented with 1.5 mM glutamine, 1 mM sodium pyruvate, 0.1 mM non-essential amino acids, 50 μM 2-mercaptoethanol, 100 IU/ml penicillin-streptomycin mixture and 10% heat-inactivated fetal bovine serum. A total of $0.5\times10^6$ B cells per ml (i.e. $0.1\times10^6$/200 μl/well) were stimulated with different concentrations of the CpG ODNs to be tested (0.03, 0.1, 0.3, 1 and 3 μM) in a 96-well flat bottom plate in triplicate for a total of 72 h. After 66 h, cells were pulsed with 0.75 ρCi of [$^3$H]-thymidine (1 Ci=37 GBq; Perkin Elmer Life Science) in 20 μl RPMI1640 medium (serum-free) per well and then harvested after 8 h. Plates were harvested using a cell harvester and radioactive incorporation was determined using standard liquid scintillation techniques. Results were shown as mean cpm+/−SD or proliferation index (cpm treated group/cpm medium control). The results were shown in FIG. 5, wherein HP3004 was a positive control.

Conclusion: The CpG ODNs can activate human PBMC cells, induce B cell proliferation, and then up-regulate the expression of costimulatory molecules and secretion of cytokines (such as IL-6, TNF-α).

Example 5 Cytokine Induction by CpG ODNs in PBMC Cultures

Figure 6:
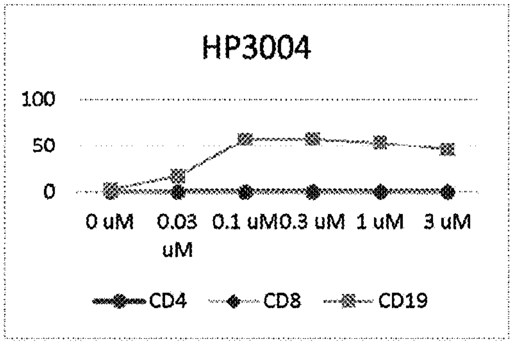
FIG. 6 shows the effect of CpG ODN in stimulating IFN-α secretion in human PBMCs.
Figure 6:
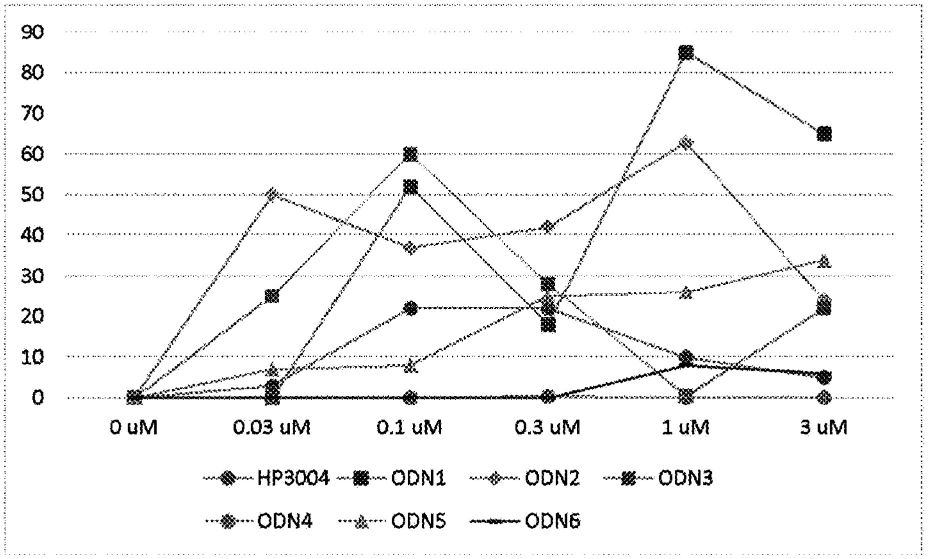
Figure 7:
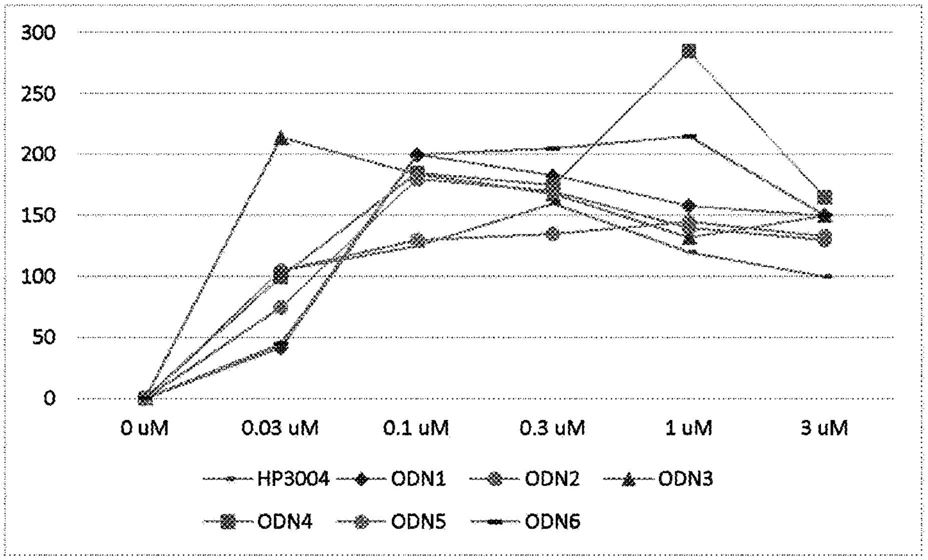
FIG. 7 shows the effect of CpG ODN in stimulating IL-6 secretion in human PBMCs.
Figure 8:
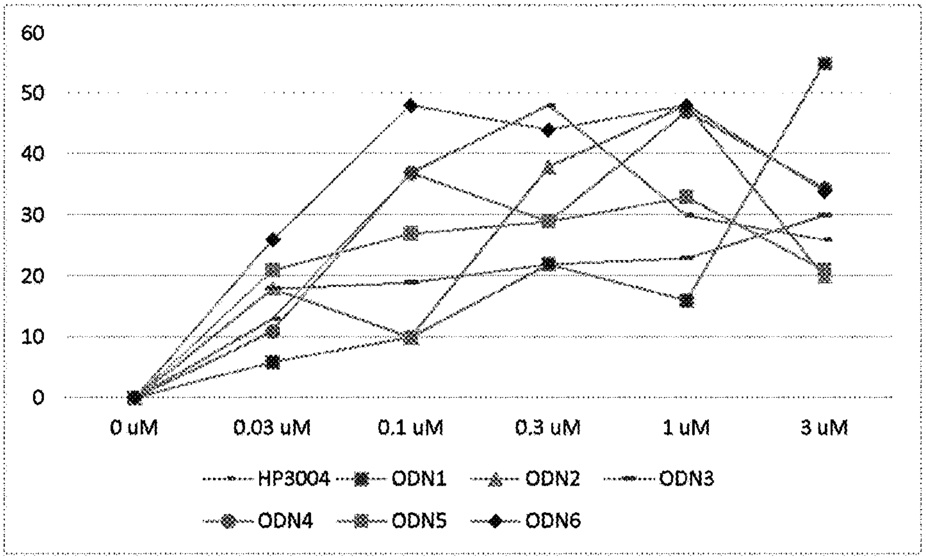
FIG. 8 shows the effect of CpG ODN in stimulating TNF-α secretion in human PBMCs.

Human PBMCs were inoculated in a 96-well plate at $5\times10^6$ cells/ml. The CpG ODNs in a phosphate buffered saline (PBS, pH 7.4; Mediatech) were added to the cell culture to a final concentration of 10.0 μg/ml. The cells were then incubated at 37° C. for 24 h and the supernatant was collected for ELISA analysis. Each experiment was performed in triplicate. Levels of IFN-α, IL-6 and TNF-α were determined by sandwich ELISA. Reagents used in the Example including anti-cytokine antibodies and standards were purchased from PharMingen. The results were shown in FIGS. 6-8.

Conclusion: The CpG ODN sequences can significantly increase the levels of IL-6 and TNF-α.

Example 6: HEK-BLUE Detection

Cell Passage

Cells were maintained and passaged in a proliferation medium supplemented with 10 μg/ml Blasticidin and 100 μg/ml Zeocin™.

Proliferation medium: DMEM, 4.5 g/L glucose, 10% (v/v) fetal bovine serum, 50 U/ml penicillin, 50 U/ml streptomycin, 100 μg/ml Normocin™, 2 mM-glutamine.

Passage Medium

| Component | Concentration | Volume (ml) |
|---|---|---|
| DMEM (with L-glutamine) | 90% | 88.6 |
| FBS Fetal Bovine Serum | 10% | 10 |
| P/S (penicillin/streptomycin)(100X) | 1% | 1 |
| Blasticidin (10 mg/ml) | 10 μg/ml | 0.1 |
| Normocin (50 mg/ml) | 100 μg/ml | 0.2 |
| Zeocin (100 mg/ml) | 100 μg/ml | 0.1 |

After reaching a density of 70%-80%, cells should be passaged and detached by tapping the ampoule or using a cell scraper after replacing the original medium with PBS. The detached cells were collected and centrifuged for 5 min. For cell count, $2\text{-}4\times10^4$ cells were inoculated in a 96-well plate, and then treated after 2-3 days.

Figure 9:
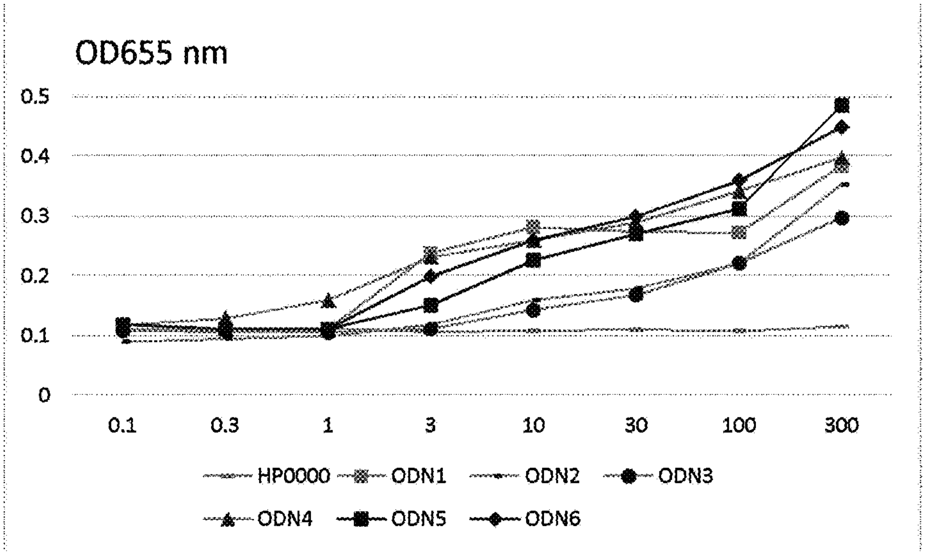
FIG. 9 shows the detection results of CpG in stimulating HEK-Blue hTLR9 cells.
Figure 10:
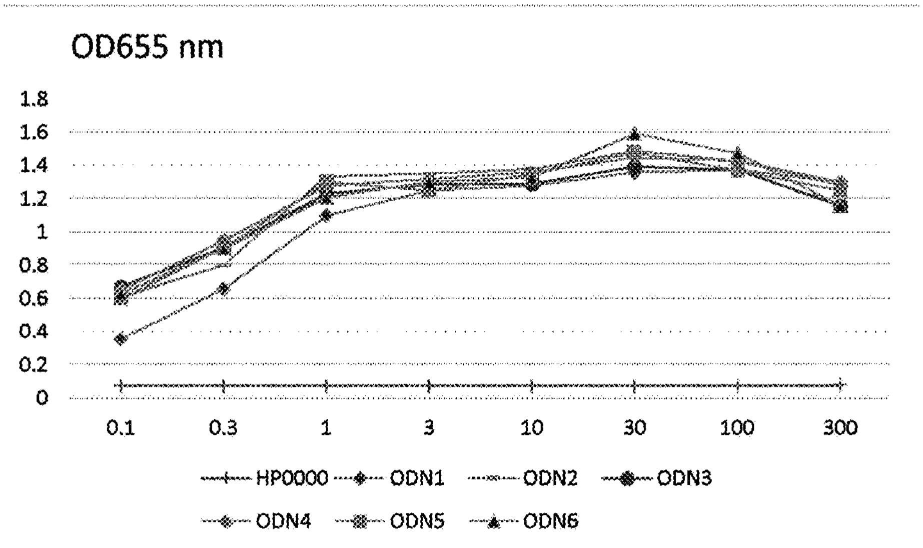
FIG. 10 shows the detection results of CpG in stimulating HEK-Blue mTLR9 cells.
Figure 11:
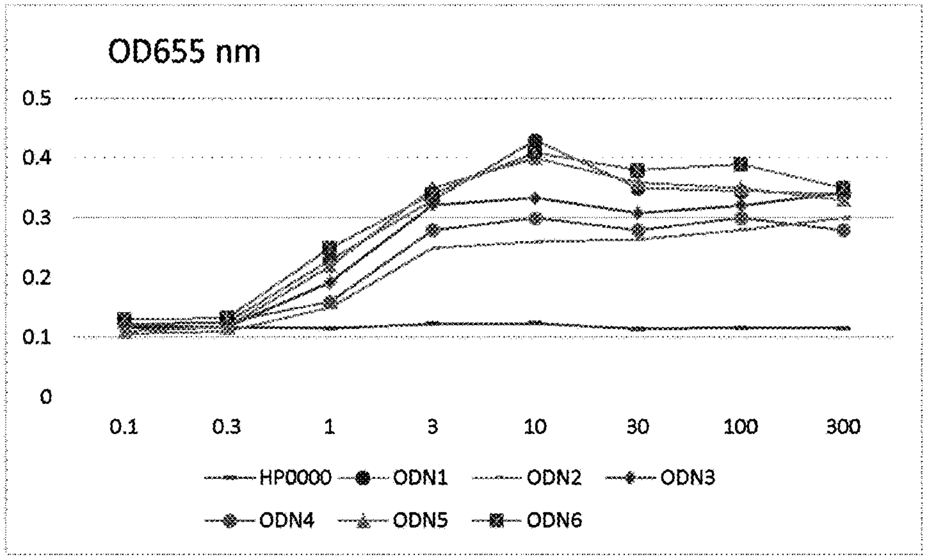
FIG. 11 shows the detection results of CpG in stimulating Ramos-Blue cells.

The predetermined final concentrations of positive control (HP3004), negative control (HP0000) and CpG ODNs were all 0.003, 0.01, 0.03, 0.1, 0.3, 1, 3, 10, 30, and 100 μg/ml, and the concentration of medium was not less than 90%. 10

μl of negative control, positive control and test substances were added to the corresponding wells. Cells were incubated for 24 h in an incubator with 5% $CO_2$. The medium was poured into a 250 ml narrow-necked flask, added with 100 ml of water, stirred evenly, and heated at 37° C. for 30 min. 50 μl of cell supernatant was taken and centrifuged for 5 min. 20 μl of the resulting supernatant and 180 μl of QUANTI-Blue were added to each well of a 96-well plate, and then incubated at 37° C. for 6 h. Absorbance at 655 nm wavelength was measured with a microplate reader. See FIGS. 9-11.

Results: As can be seen from FIGS. 9-11, the CpG ODNs had a good effect on the activity of HEK-Blue hTLR9 cells, HEK-Blue mTLR9 cells and Ramos-Blue cells.

Figure 12:
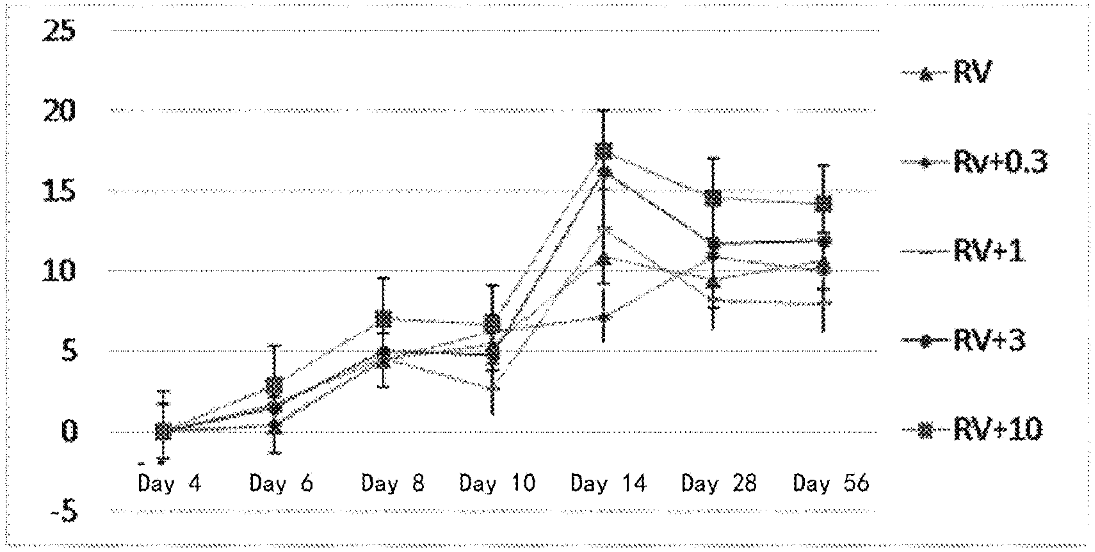
FIG. 12 shows the effect of ODN3 on rabies virus-neutralizing antibody titers.

Example 7: The Effect of the Combination of ODN3 and Rabies Vaccine on the Titers of Anti-Rabies Virus Neutralizing Antibody in Mice The mice were divided into 8 groups, with 8 mice in each group. The background serum of each group of mice was collected 2 days before immunization. The vaccine was injected (intramuscularly) at day 0, day 3 and day 7. On day 4, day 6, day 8, day 10, day 14, day 28 and day 56, eyeballs were removed and blood was collected, and the serum was separated. The titers of anti-rabies virus neutralizing antibodies in mouse serum were determined one by one using the RFFIT method. The results were shown in FIG. 12.

The specific groupings were as follows:

| Group | Treatment | Number |
|---|---|---|
| RV | 0.1 ml vero vaccine | 8 |
| RV + 0.3 | 0.1 ml vero vaccine + 0.3 μg/mouse CpG | 8 |
| RV + 1 | 0.1 ml vero vaccine + 1 μg/mouse CpG | 8 |
| RV + 3 | 0.1 ml vero vaccine + 3 μg/mouse CpG | 8 |
| RV + 10 | 0.1 ml vero vaccine + 10 μg/mouse CpG | 8 |
| ½RV + 1 | ½ × 0.1 ml vero vaccine + 1 μg/mouse CpG | 8 |
| ¼RV + 1 | ¼ × 0.1 ml vero vaccine + 1 μg/mouse CpG | 8 |
| ⅛RV + 1 | ⅛ × 0.1 ml vero vaccine + 1 μg/mouse CpG | 8 |

Results: As can be seen from FIG. 12, in the group of combination of rabies vaccine and different doses of ODN3, the level of antibodies produced changed over time, but the overall trend showed an increase. The antibody levels in rabies vaccine+1 μg ODN3 group (RV+1), rabies vaccine+3 μg ODN3 group (RV+3), and rabies vaccine+10 μg ODN3 group (RV+10) were higher than that in vaccine without adjuvant group (RV). After 14 days of immunization, the antibody levels of the four groups (rabies vaccine, rabies vaccine+1 μg ODN3, rabies vaccine+3 μg ODN3, and rabies vaccine+10 μg ODN3) reached the peak, and then fell back. Among them, the rabies vaccine+10 μg ODN3 group had the highest antibody level during all of the detection times. Based on the time of the neutralizing antibody production, the peak and the continuity of the neutralizing antibody, the experimental results of the 10 μg ODN3 group were better than the other dose groups.

Example 8 Comparison of Different Doses of ODN3 to Enhance the Effect of Rabies Vaccine to Induce Antibody Production 112 mice (56 females and 56 males, 18-22 grams of body weight/mice), rabies vaccine (1 ml/dose) (containing 2.5 IU), and ODN3 were used in the Example. The mice were grouped with 8 mice in each group (four males and four females). Vaccine groups: Rabies vaccine, Rabies vaccine+0.3 μg ODN3, rabies vaccine+1 μg ODN3, rabies vaccine+3 μg ODN3, and rabies vaccine+10 μg ODN3. The Rabies vaccines and CpG ODN were all dissolved in PBS. On day 0, day 3, day 7, day 14 and day 28, the mice were immunized respectively according to different groups. The immunization was carried out by intraperitoneal injection. After 4, 6, and 8 days of immunization, blood was collected from the tail vein of the mice, and the serum was separated. The rabies vaccine antibody titer in the serum of the mice was detected by rapid fluorescent focus inhibition test (RFFIT) for rabies vaccines. Blood was collected from the tail vein of mice two days before immunization, and the obtained serum was used as a negative control.

Figure 13:
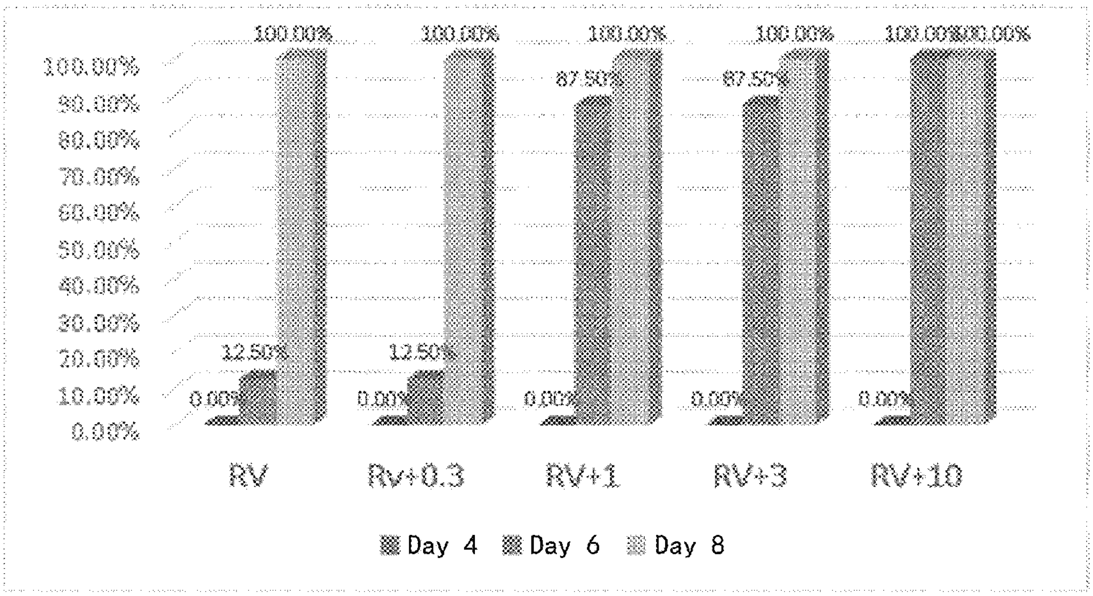
FIG. 13 shows the immune enhancing effect of different dosages of ODN3 in combination with rabies vaccine.

Results: the immune effect of rabies vaccine in each group was enhanced over time; with the increase of the dose of ODN3, the immune effect of rabies vaccine was enhanced. The results were shown in FIG. 13.

Conclusion: ODN3 can significantly increase the immune effect of rabies vaccine.

Example 9 ODN3 is Used as Rabies Vaccine Adjuvant to Reduce the Dosage of Rabies Vaccine 128 mice (64 males and 64 females, body weight 18-22 grams/mice) and rabies vaccine (1 ml/dose) (containing 2.5 IU) were used. The mice were grouped with 8 mice in each group (4 males and 4 females). Vaccine groups: Rabies vaccine, rabies vaccine+1 μg ODN3, ½ rabies vaccine+1 μg ODN3, ¼ rabies vaccine+1 μg ODN3, and ⅛ rabies vaccine+1 μg ODN3.

The above rabies vaccines and ODN3 all were dissolved in PBS. Immunization of mice: On day 0, day 3, day 7, day 14 and day 21, the mice were immunized respectively according to different groups. The immunization was carried out by intraperitoneal injection. On day 28, blood was collected from the tail vein of the mice, and the serum was separated. The rabies vaccine antibody titer in the serum of the mice was detected by the rapid fluorescence focus inhibition test (RFFIT) for rabies vaccines. Blood was collected from the tail vein of mice two days before immunization, and the obtained serum was used as a negative control.

Figure 14:
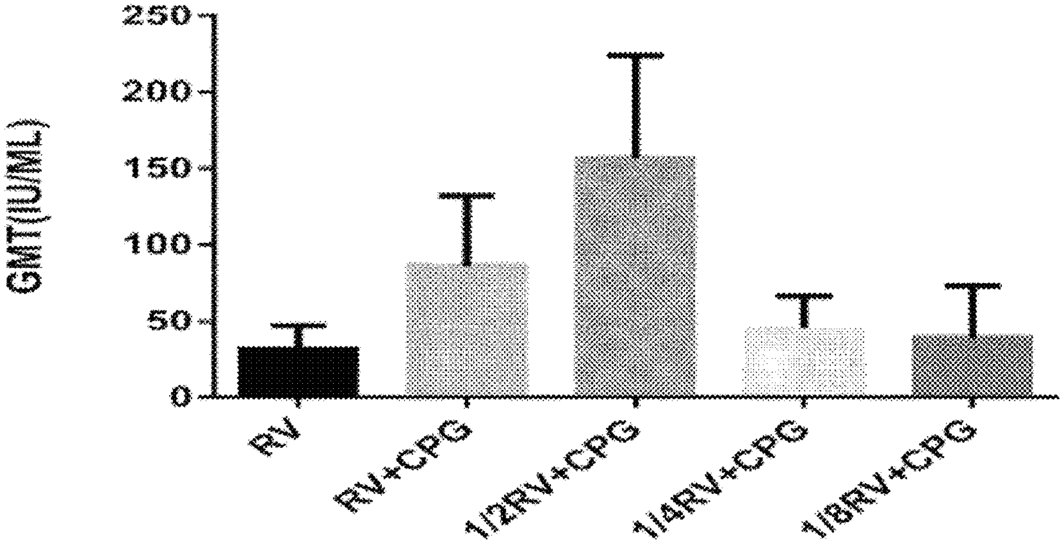
FIG. 14 shows the immune enhancing effect of different dosages of rabies vaccine in combination with ODN3.

Results: the combination of rabies vaccine in reduced dosage with ODN3 can still stimulate the mice to produce high levels of rabies virus-specific antibodies. The antibody titers (GMT) in the groups of rabies vaccine+1 μg ODN3, ½ rabies vaccine+1 μg ODN3, ¼ rabies vaccine+1 μg ODN3 and ⅛ rabies vaccine+1 μg ODN3 can all achieve higher levels than that when rabies vaccine was used alone, indicating that the CpG ODN can reduce the dosage of rabies vaccine. The results are shown in FIG. 14.

Conclusion: ODN3 can reduce the dosage of rabies vaccine.

Example 10 Different CpG ODN Sequences Used as Rabies Vaccine Adjuvants

Figure 15:
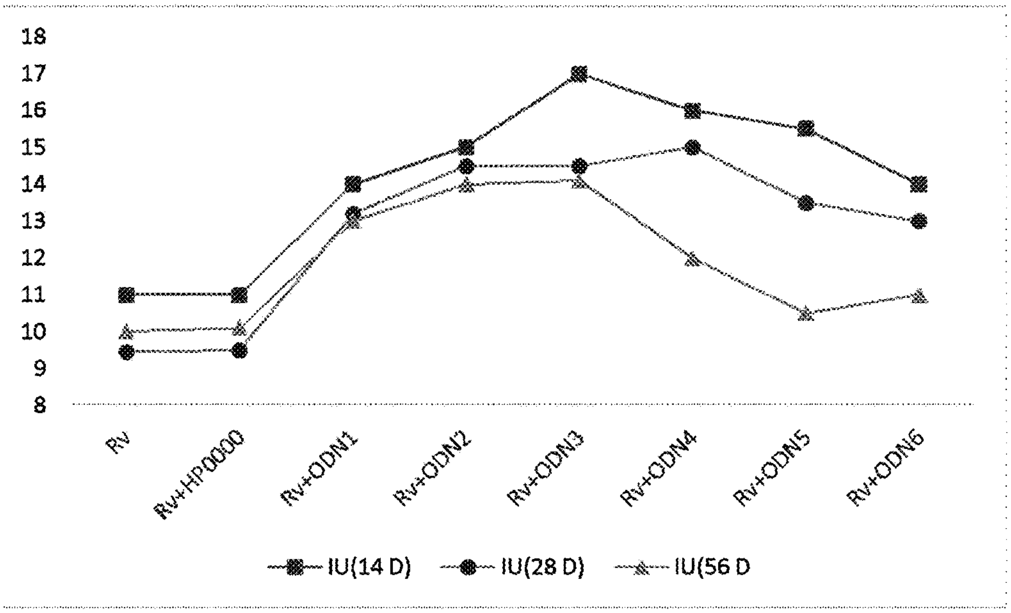
FIG. 15 shows the effect of combinations of different CpG ODNs with rabies vaccine on rabies virus-neutralizing antibody titers.

BALB/c mice were randomly divided into eight groups: human rabies vaccine group, human rabies vaccine+ODN1 (10 μg/mouse) group, human rabies vaccine+ODN2 (10 μg/mouse) group, human rabies vaccine+ODN3 (10 μg/mouse) group, human rabies vaccine+ODN4 (10 μg/mouse) group, human rabies vaccine+ODN5 (10 μg/mouse) group, human rabies vaccine+ODN6 (10 μg/mouse) group, human rabies vaccine+HP0000 (10 μg/mouse) group. Each group was immunized three times on day 0, day 7, and day 21 respectively through hindlimb muscles, and the dosage of each immunization was 0.2 ml/mouse. On day 14, day 28 and day 56 after immunization, the eyeballs were removed and blood was collected, the serum was separated, the content of anti-rabies virus antibody in serum was detected, and the neutralizing antibody titer was shown in FIG. 15.

Conclusion: the CpG ODNs can increase the level of antibody titer.

Figure 16:
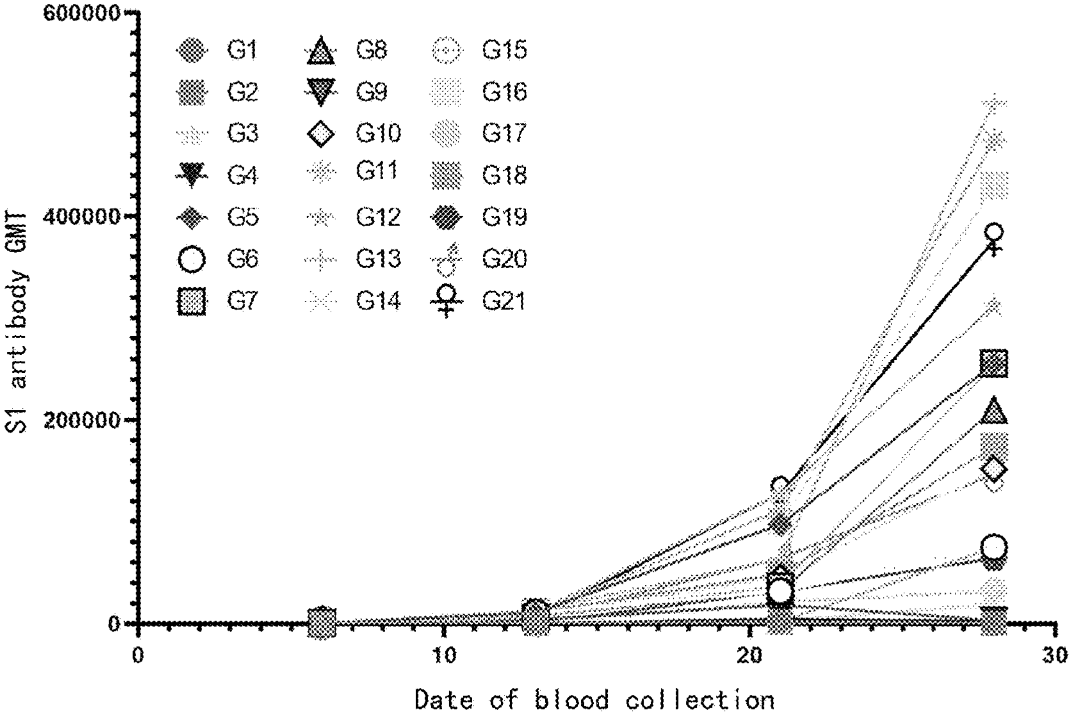
FIG. 16 shows the effect of ODN6 in combination with the inactivated SARS-COV-2 vaccine on the titer of mouse anti-SARS-CoV-2 S protein-specific IgG antibody at D6-28.
Figure 17:
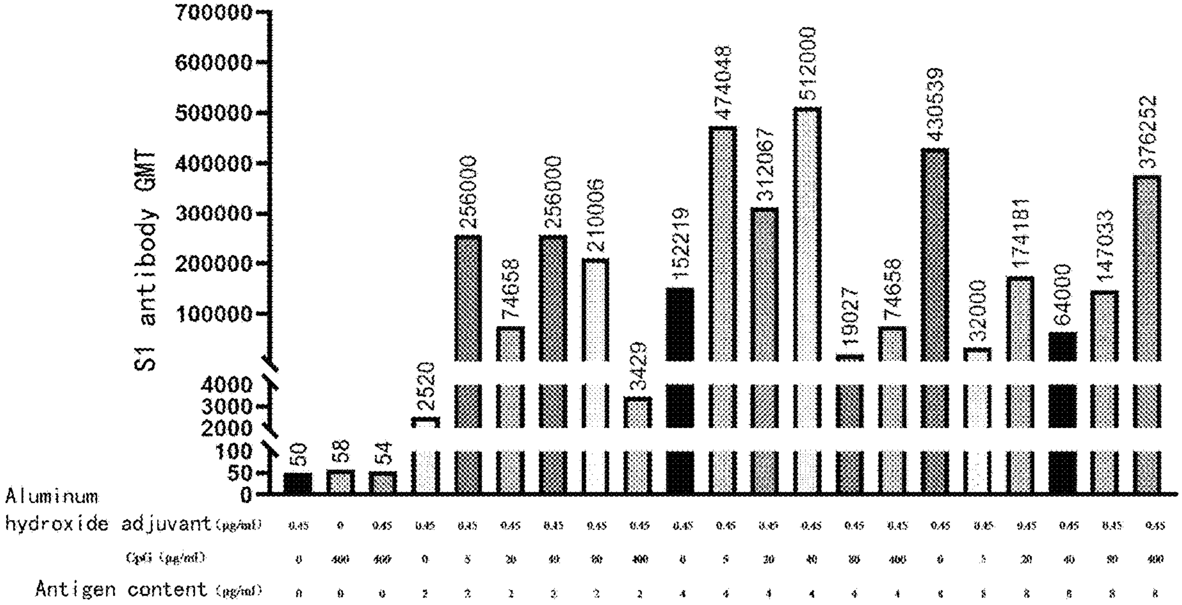
FIG. 17 shows the effect of ODN6 in combination with the inactivated SARS-COV-2 vaccine on the titer of mouse anti-SARS-CoV-2 S protein-specific IgG antibody at D28.
Figure 18:
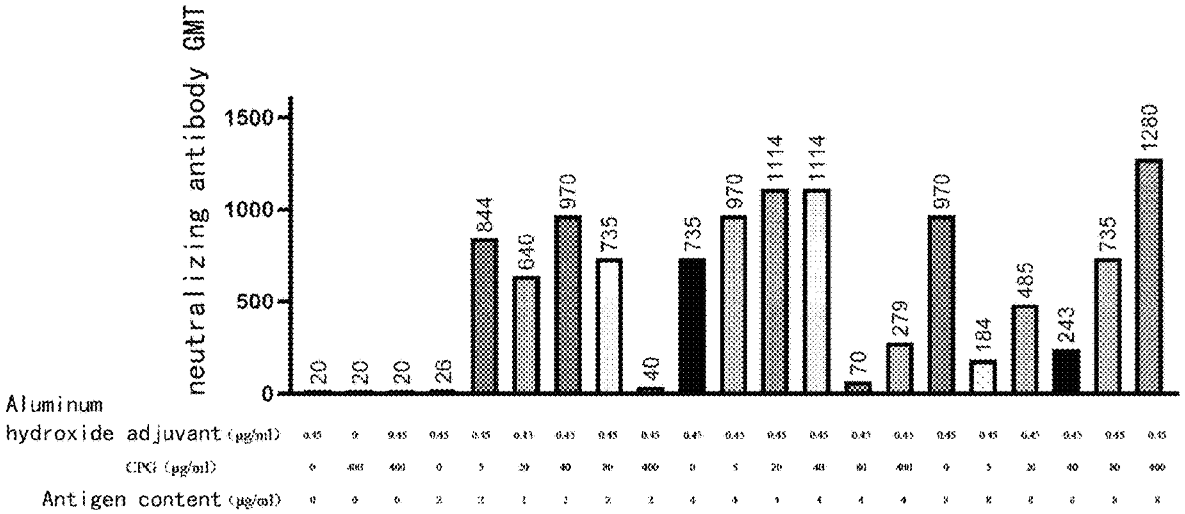
FIG. 18 shows the effect of ODN6 in combination with the inactivated SARS-COV-2 vaccine on mouse anti-SARS-CoV-2-neutralizing antibody titers.

Example 11: Effects of ODN6 in Combination with Inactivated SARS-COV-2 Vaccine on the Titers of Anti-SARS-CoV-2 S Protein-Specific IgG and Virus-Neutralizing Antibody in Mice 18-20 g BALB/c mice were selected and grouped with 9 or 10 mice in each group (half female and half male); each group was immunized by intraperitoneal injection on DO and D14 according to designed immunization program, with 0.5 ml per injection. According to the designed time, blood was collected on DO, D6, D13, D21 and D28 to separate serum, and all the sera were tested for S protein-specific IgGs and virus-neutralizing antibodies; the geometric mean titers of serum IgGs and virus-neutralizing antibodies of each group were statistically calculated. The results were shown in FIGS. 16-18.

The specific groupings were as follows:

| group | antigen content (μg/ml) | Aluminum content (μg/ml) | CpG content (μg/ml) | Number of immunized mice (mouse) |
|---|---|---|---|---|
| 1 | 0 | 450 | 0 | 9 |
| 2 | | 0 | 400 | 9 |
| 3 | | 450 | 400 | 9 |
| 4 | 2 | 450 | 0 | 9 |
| 5 | | 450 | 5 | 9 |
| 6 | | 450 | 20 | 9 |
| 7 | | 450 | 40 | 9 |
| 8 | | 450 | 80 | 9 |
| 9 | | 450 | 400 | 9 |
| 10 | 4 | 450 | 0 | 9 |
| 11 | | 450 | 5 | 9 |
| 12 | | 450 | 20 | 9 |
| 13 | | 450 | 40 | 9 |
| 14 | | 450 | 80 | 9 |
| 15 | | 450 | 400 | 9 |
| 16 | 8 | 450 | 0 | 9 |
| 17 | | 450 | 5 | 9 |
| 18 | | 450 | 20 | 9 |
| 19 | | 450 | 40 | 9 |
| 20 | | 450 | 80 | 9 |
| 21 | | 450 | 400 | 9 |

Results: As can be seen from FIGS. 16-18, the antigen-specific S1 antibody was hardly detected in the double-adjuvant control group on D28; except for the relatively lower S1 antibody levels in groups of 2 μg/mL antigen+450 μg/mL aluminum hydroxide adjuvant group, and 2 μg/mL antigen+450 μg/mL aluminum hydroxide adjuvant+400 μg/mL CpG group, other groups induced higher S1 antibody titers. As can be seen from the results of neutralizing antibody titers in serum of mice in each group, except for the relatively lower neutralizing antibody levels in groups of 2 μg/mL antigen+450 μg/mL aluminum hydroxide adjuvant group, 2 μg/mL antigen+450 μg/mL aluminum hydroxide adjuvan+400 μg/mL CpG group and 4 μg/mL antigen+450 μg/mL aluminum hydroxide adjuvant+80 μg/mL CpG group, other groups induced higher titers of neutralizing antibody.

CONCLUSION: The combination of inactivated SARS-COV-2 vaccine with ODN6 and aluminum adjuvant can induce higher titers of SARS-CoV-2 S protein-specific IgG and virus-neutralizing antibody. On D28, the 4 μg/mL antigen+450 μg/mL aluminum hydroxide adjuvant+40 μg/mL CpG group induced the highest S1 antibody titer. The 8 μg/mL antigen+450 μg/mL aluminum hydroxide adjuvant+400 μg/mL CpG group induced the highest neutralizing antibody titer.

EQUIVALENT TECHNICAL SOLUTIONS

The specific Examples described above further describe the purpose, technical solutions and beneficial effects of the present invention in detail, but they should not be construed as limiting the scope of the invention. It should be noted that any modifications, equivalent replacements and improvements made by those skilled in the art within the spirit and scope of the invention should be included within the protection scope of the present invention.

We claim:

1. An immunoregulatory CpG ODN with a maximum length of 26 bp comprising a nucleotide sequence selected from SEQ ID NOs: 1-4 and 6, wherein at least one nucleotide in the nucleotide sequence is a phosphorothioated nucleotide.

2. The immunoregulatory CpG ODN of claim 1, wherein the immunoregulatory CpG ODN consists of a nucleotide sequence selected from the group consisting of SEQ ID NOs: 1-4 and 6, and wherein the nucleotide sequence is a completely-phosphorothioated nucleotide sequence.

3. A method of preventing or treating tumors, microbial infections or allergies in a subject, wherein the method comprises administering an effective amount of the immunoregulatory CpG ODN of claim 1 to the subject.

4. The method of claim 3, wherein the subject is a human or an animal, wherein the animal is a mouse, a rat, a domestic animal, or a domestic bird.

5. A pharmaceutical composition comprising the immunoregulatory CpG ODN of claim 1 and a pharmaceutically acceptable carrier.

6. A method of preventing or treating tumors, microbial infections or allergies in a subject, wherein the method comprises administering an effective amount of the pharmaceutical composition of claim 5 to the subject.

7. A vaccine adjuvant comprising the immunoregulatory CpG ODN of claim 1.

8. The vaccine adjuvant of claim 7, further comprising one or more other adjuvants selected from the group consisting of insoluble aluminum salt colloids, oil-water emulsions, microorganisms and their metabolites, nucleic acids and the analogs thereof, cytokines, immunostimulatory complexes, propolis, or liposomes.

9. A vaccine comprising the immunoregulatory CpG ODN of claim 1 and an antigen, wherein the antigen is a rabies antigen or a SARS-COV-2 antigen.

10. The vaccine of claim 9, wherein the vaccine is a rabies vaccine for a human or an animal, and the immunoregulatory CpG ODN consists of a nucleotide sequence as set forth in SEQ ID NO: 3, wherein the nucleotide sequence is a completely-phosphorothioated nucleotide sequence, and the concentration of the CpG ODN is 0.01 μg/ml-1000 μg/ml.

11. The vaccine of claim 9, wherein the vaccine is a SARS-COV-2 vaccine, and wherein the vaccine further comprises an aluminum adjuvant.

12. The vaccine of claim 11, wherein the immunoregulatory CpG ODN consists of a nucleotide sequence as set forth in SEQ ID NO: 6, and wherein the nucleotide sequence is a completely-phosphorothioated nucleotide sequence.

13. The vaccine of claim 10, wherein the concentration of the CpG ODN is 1 μg/ml-10 μg/ml.

14. The vaccine of claim 11, wherein the aluminum adjuvant is aluminum hydroxide adjuvant.

15. The vaccine of claim 11, wherein the vaccine is an inactivated SARS-COV-2 vaccine.

16. The vaccine of claim 14, wherein the concentration of the antigen is 1 μg/mL-10 g/mL; the concentration of the aluminum hydroxide adjuvant is 1 μg/mL-1000 μg/mL; and the concentration of the immunoregulatory CpG ODN is 1 μg/mL-1000 μg/mL.

17. A rabies vaccine comprising the vaccine adjuvant of claim 7.

18. The rabies vaccine of claim 17, wherein the concentration of CpG ODN in the rabies vaccine is 0.01 μg/ml-1000 μg/ml.

19. The rabies vaccine of claim 17, wherein the concentration of CpG ODN in the rabies vaccine is 1 μg/ml-10 μg/ml.

20. A SARS-COV-2 vaccine comprising the vaccine adjuvant of claim 7.

21. The SARS-COV-2 vaccine of claim 20, wherein the SARS-COV-2 vaccine is an inactivated SARS-COV-2 vaccine, and the concentration of CpG ODN in the SARS-COV-2 vaccine is 0.01 μg/ml-1000 μg/ml.

22. The SARS-COV-2 vaccine of claim 20, wherein the SARS-COV-2 vaccine is an inactivated SARS-COV-2 vaccine, and the concentration of CpG ODN in the SARS-COV-2 vaccine is 1 μg/ml-10 μg/ml.

* * * * *

SEQUENCE LISTING

```
<160> NUMBER OF SEQ ID NOS: 8

<210> SEQ ID NO 1
<211> LENGTH: 26
<212> TYPE: DNA
<213> ORGANISM: artificial sequence
<220> FEATURE:
<223> OTHER INFORMATION: artificially synthesized nucleotide sequence

<400> SEQUENCE: 1

tcgcgacgtt cgcgggacgt tcccta                                          26


<210> SEQ ID NO 2
<211> LENGTH: 26
<212> TYPE: DNA
<213> ORGANISM: artificial sequence
<220> FEATURE:
<223> OTHER INFORMATION: artificially synthesized nucleotide sequence
```

<400> SEQUENCE: 2
tcgcgacgtt cgcgcgacgt tcgcta 26

<210> SEQ ID NO 3
<211> LENGTH: 24
<212> TYPE: DNA
<213> ORGANISM: artificial sequence
<220> FEATURE:
<223> OTHER INFORMATION: artificially synthesized nucleotide sequence

<400> SEQUENCE: 3
tcgcgacgtt cgccgacgtt cgta 24

<210> SEQ ID NO 4
<211> LENGTH: 23
<212> TYPE: DNA
<213> ORGANISM: artificial sequence
<220> FEATURE:
<223> OTHER INFORMATION: artificially synthesized nucleotide sequence

<400> SEQUENCE: 4
tggacgttcg tcgttcgtcc ttc 23

<210> SEQ ID NO 5
<211> LENGTH: 23
<212> TYPE: DNA
<213> ORGANISM: artificial sequence
<220> FEATURE:
<223> OTHER INFORMATION: artificially synthesized nucleotide sequence

<400> SEQUENCE: 5
tcgtcgttcg tcgttcgacg ttc 23

<210> SEQ ID NO 6
<211> LENGTH: 23
<212> TYPE: DNA
<213> ORGANISM: artificial sequence
<220> FEATURE:
<223> OTHER INFORMATION: artificially synthesized nucleotide sequence

<400> SEQUENCE: 6
tcgaggttcg tcgttcctcg ttc 23

<210> SEQ ID NO 7
<211> LENGTH: 22
<212> TYPE: DNA
<213> ORGANISM: artificial sequence
<220> FEATURE:
<223> OTHER INFORMATION: artificially synthesized nucleotide sequence

<400> SEQUENCE: 7
tgactgtgaa cgttcgagat ga 22

<210> SEQ ID NO 8
<211> LENGTH: 29
<212> TYPE: DNA
<213> ORGANISM: artificial sequence
<220> FEATURE:
<223> OTHER INFORMATION: artificially synthesized nucleotide sequence

<400> SEQUENCE: 8
tggccaagct tgggcccctt gcaagggcc 29